United States Patent
Liu et al.

(10) Patent No.: US 11,504,425 B2
(45) Date of Patent: Nov. 22, 2022

(54) AMPHIPHILIC OLIGODEOXYNUCLEOTIDE CONJUGATES AS ADJUVANT ENHANCERS

(71) Applicant: WAYNE STATE UNIVERSITY, Detroit, MI (US)

(72) Inventors: Haipeng Liu, Troy, MI (US); Chunsong Yu, Detroit, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/795,953

(22) Filed: Feb. 20, 2020

(65) Prior Publication Data

US 2020/0268879 A1    Aug. 27, 2020

Related U.S. Application Data

(60) Provisional application No. 62/810,844, filed on Feb. 26, 2019.

(51) Int. Cl.
| | |
|---|---|
| *C07H 21/04* | (2006.01) |
| *A61K 39/39* | (2006.01) |
| *A61K 47/54* | (2017.01) |
| *C12N 15/117* | (2010.01) |
| *A61K 39/00* | (2006.01) |

(52) U.S. Cl.
CPC ............ *A61K 39/39* (2013.01); *A61K 47/543* (2017.08); *A61K 47/549* (2017.08); *A61K 47/554* (2017.08); *C12N 15/117* (2013.01); *A61K 2039/55511* (2013.01); *A61K 2039/55561* (2013.01); *A61K 2039/575* (2013.01); *C12N 2310/17* (2013.01); *C12N 2310/315* (2013.01); *C12N 2310/3515* (2013.01)

(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 9,107,904 | B2 | 8/2015 | Irvine et al. |
| 9,347,064 | B2 | 5/2016 | Barrat et al. |
| 10,029,016 | B2 | 7/2018 | Irvine et al. |
| 2007/0275047 | A1 | 11/2007 | Pfeiffer et al. |
| 2013/0156814 | A1 | 6/2013 | Barrat et al. |
| 2019/0015522 | A1 | 1/2019 | Irvine et al. |
| 2019/0023687 | A1 | 1/2019 | Sherer et al. |

FOREIGN PATENT DOCUMENTS

| | | |
|---|---|---|
| EP | 2833918 B1 | 5/2019 |
| WO | WO2006063072 A2 | 6/2006 |
| WO | WO2007038720 A2 | 4/2007 |

OTHER PUBLICATIONS

Yu, C., An, M., Jones, E. et al. Targeting Suppressive Oligonucleotide to Lymph Nodes Inhibits Toll-like Receptor-9-Mediated Activation of Adaptive Immunity. Pharm Res 35, 56 (2018). https://doi.org/10.1007/s11095-018-2344-2.*

"Tetramer Staining Guide," Medical & Biological Laboratories Co. Ltd, 2014, 29 pages.

Ahn and Huang, "Imiquimod in the Treatment of Cutaneous Warts: An Evidence-Based Review," Am. J. Clin. Dermatol., vol. 15, No. 5, 2014, pp. 387-399.

Allahyari and Mohit, "Peptide/protein Vaccine Delivery System Based on PLGA Particles," Hum. Vaccine Immunother., vol. 12, No. 3, 2016, pp. 806-828.

Anwar, et al., "Recent Clinical Trends in Toll-like Receptor Targeting Therapeutics," Med. Res. Rev., vol. 39, No. 3, 2019, pp. 1053-1090.

Ballas, et al., "Divergent Therapeutic and Immunologic Effects of Oligodeoxynucleotides With Distinct CpG Motifs," J. Immunol., vol. 167, No. 9, 2001, pp. 4878-4886.

Barrat, et al., "Nucleic Acids of Mammalian Origin Can Act as Endogenous Ligands for Toll-like Receptors and May Promote Systemic Lupus Erythematosus," J. Exp Med., vol. 202, No. 8, 2005, pp. 1131-1139.

Duthie, et al., "Use of defined TLR ligands as adjuvants within human vaccines," Immunol. Rev., vol. 239, No. 1, 2011, pp. 178-196.

Gorden, et al., "Cutting Edge: Activation of Murine TLR8 by a Combination of Imidazoquinoline Immune Response Modifiers and polyT Oligodeoxynucleotides," J. Immunol., vol. 177, No. 10, 2006, pp. 6584-6587.

Gorden, et al., "Oligodeoxynucleotides Differentially Modulate Activation of TLR7 and TLR8 by Imidazoquinolines," J. Immunol., vol. 177, No. 11, 2006, pp. 8164-8170.

Gursel, et al., "Repetitive Elements in Mammalian Telomeres Suppress Bacterial DNA-induced Immune Activation," J. Immunol., vol. 171, No. 3, 2003, pp. 1393-1400.

Hosseinzadeh and Bolhassani, "Immunostimulant Properties of Chemical Delivery Systems in Vaccine Development," Curr. Drug Deliv., vol. 12, No. 4, 2015, pp. 360-368.

Irby, et al., "Lipid-Drug Conjugate for Enhancing Drug Delivery," Mol. Pharm., vol. 14, No. 5, 2017, pp. 1325-1338.

Irvine, et al., "Synthetic Nanoparticles for Vaccines and Immunotherapy," Chem. Rev., vol. 115, No. 19, 2015, pp. 11109-11146.

(Continued)

*Primary Examiner* — Kimberly Chong
(74) *Attorney, Agent, or Firm* — Tanya M. Harding; Lee & Hayes, P.C.

(57) ABSTRACT

Amphiphilic oligonucleotide conjugates that enhance adjuvant function are disclosed. The conjugates typically include: a lipophilic component, and conjugated thereto (directly or indirectly) an immunomodulating oligonucleotide that, if it were not conjugated to the lipophilic component, would suppress TLR7 and/or TLR8 stimulation. In the presence of albumin, these conjugates significantly enhance adjuvant function, in particular the function of TLR7/8-mediated adjuvants such as an imidazoquinolinamine. The conjugates can be administered, along with an adjuvant compound, to a subject in order to cause and/or enhance an immune response (for instance, to an infectious agent or a cancer antigen) in the subject.

22 Claims, 25 Drawing Sheets

Specification includes a Sequence Listing.

(56) References Cited

OTHER PUBLICATIONS

Jurk, et al., "Modulating Responsiveness of Human TLR7 and 8 to Small Molecule Ligands With T-rich Phosphorothiate Oligodeoxynucleotides," Eur J. Immunol, vol. 36, No. 7, 2006, pp. 1815-1826.

Kozlovskaya, et al., "Encapsulation and Surface Engineering of Pancreatic Islets: Advances and Challenges," retrieved at <www.intechopen.com>. Biomedicine, 2012, 34 pages.

Li and Guo, "Recent Advances in Toll Like Receptor-Targeting Glycoconjugate Vaccines," Molecules, vol. 23, No. 7, 2018, 24 pages.

Liu, et al., "Structure-based Programming of Lymph Node Targeting in Molecular Vaccines," Nature, vol. 507, No. 7493, 2014, pp. 519-522.

Lynn, et al., "In vivo characterization of the physicochemical properties of TLR agonist delivery that enhance vaccine immunogenicity," Nat Biotechnol, vol. 33, No. 11, 2015, pp. 1201-1210.

Shao, et al., "Nanoparticle-Based Immunotherapy for Cancer," American Chemical Society, vol. 9, No. 1, 2015, pp. 16-30.

Stunz, et al., "Inhibitory Oligonucleotides Specifically Block Effects of Stimulatory CpG Oligonucleotides in B Cells," Eur. J Immunol, vol. 32, No. 5, 2002, pp. 1212-1222.

Van Seters, et al., "Treatment of Vulvar Intraepithelial Neoplasia With Topical Imiquimod," N. Eng. J. Med., vol. 358, No. 14, 2008, pp. 1465-1473.

Winkler, "Oligonucleotide conjugates for therapeutic applications," Ther. Deliv., vol. 4, No. 7, 2013, pp. 791-809.

Yu, et al., "Targeting Suppressive Oligonucleotide to Lymph Nodes Inhibits Toll-like Receptor-9-Mediated Activation of Adaptive Immunity," Pharm Res., vol. 35, No. 3, 2018, 17 pages.

Zhang, et al., "Structural Analysis Reveals That Toll-like Receptor 7 Is a Dual Receptor for Guanosine and Single-Stranded RNA," Immunity, vol. 45, No. 4, 2016, pp. 737-748.

\* cited by examiner

Imiquimod
(IMQ; R837)

Resiquimod
(R848)

Gardiquimod

IRS 954: 5'-tgctcctgggagggttgt-3'
Lipo IRS 954: 5'-L-tgctcctgggagggttgt-3'

T20: 5'-tttttttttttttttttttt-3'

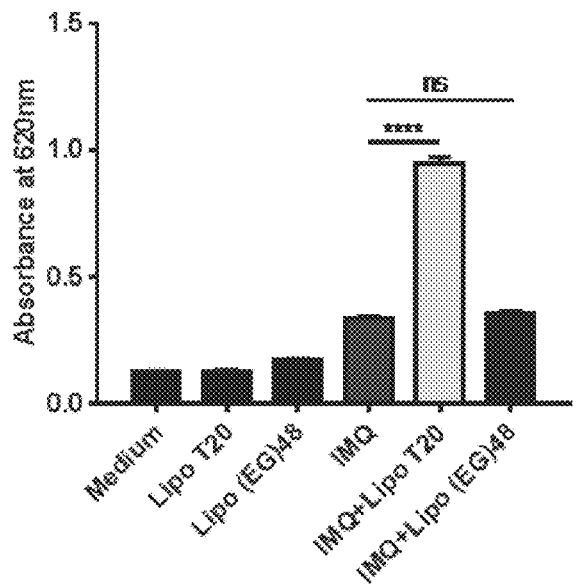
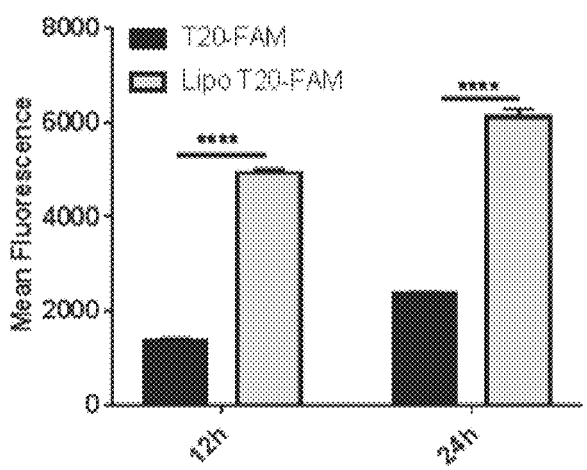
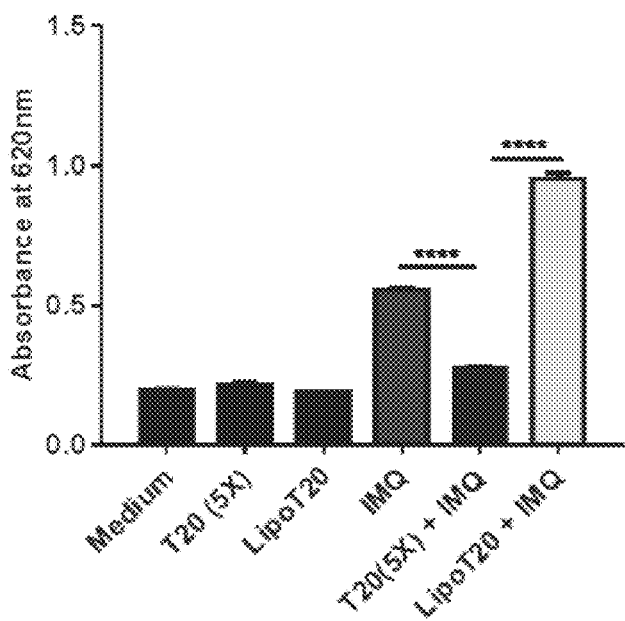

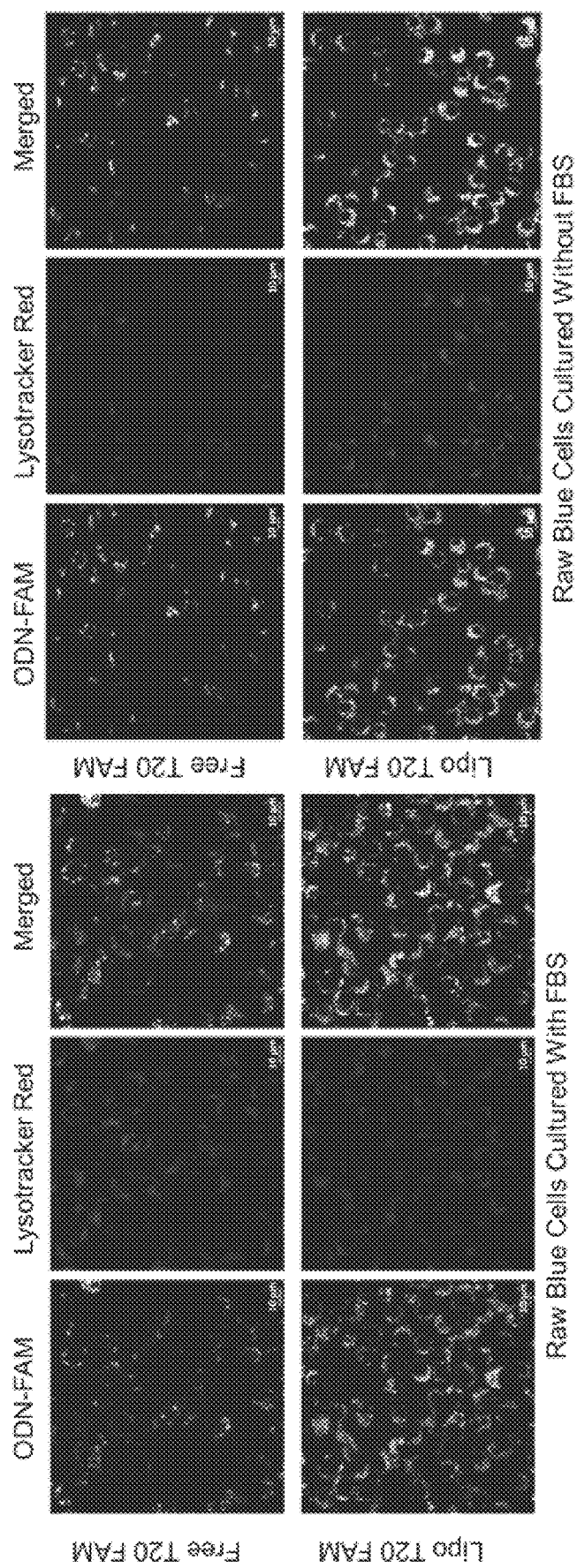

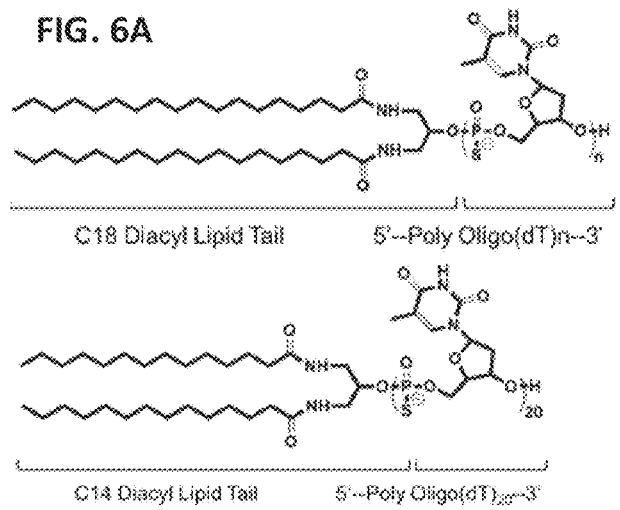
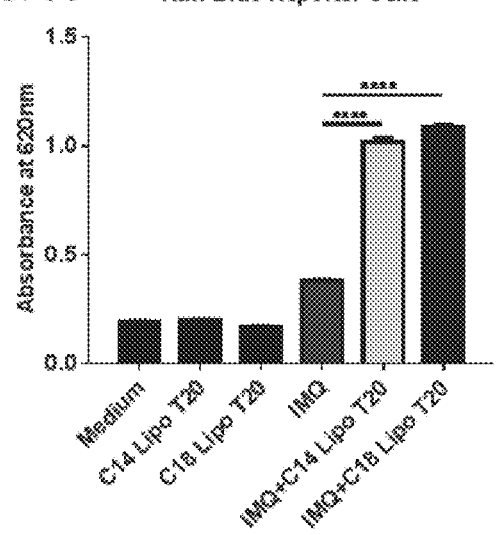
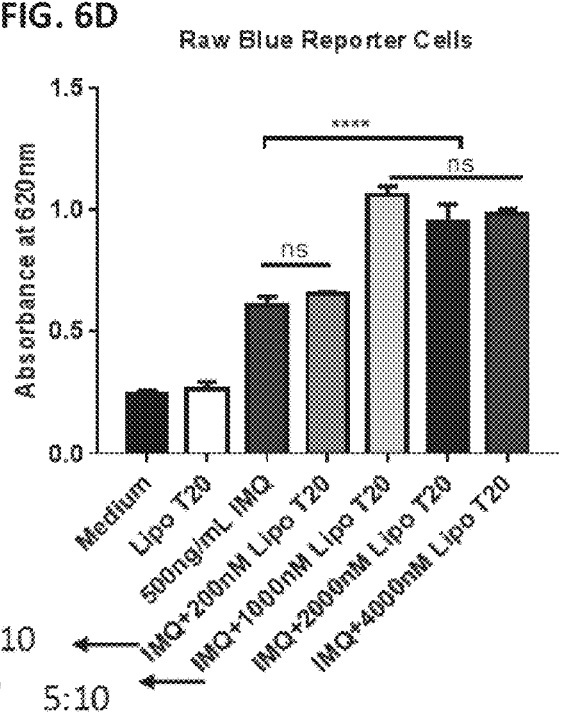
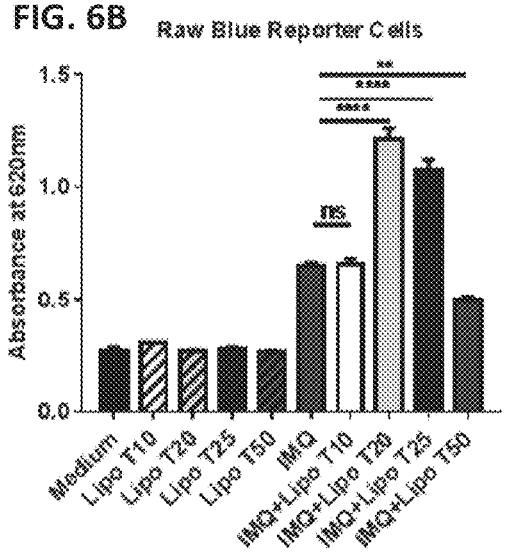

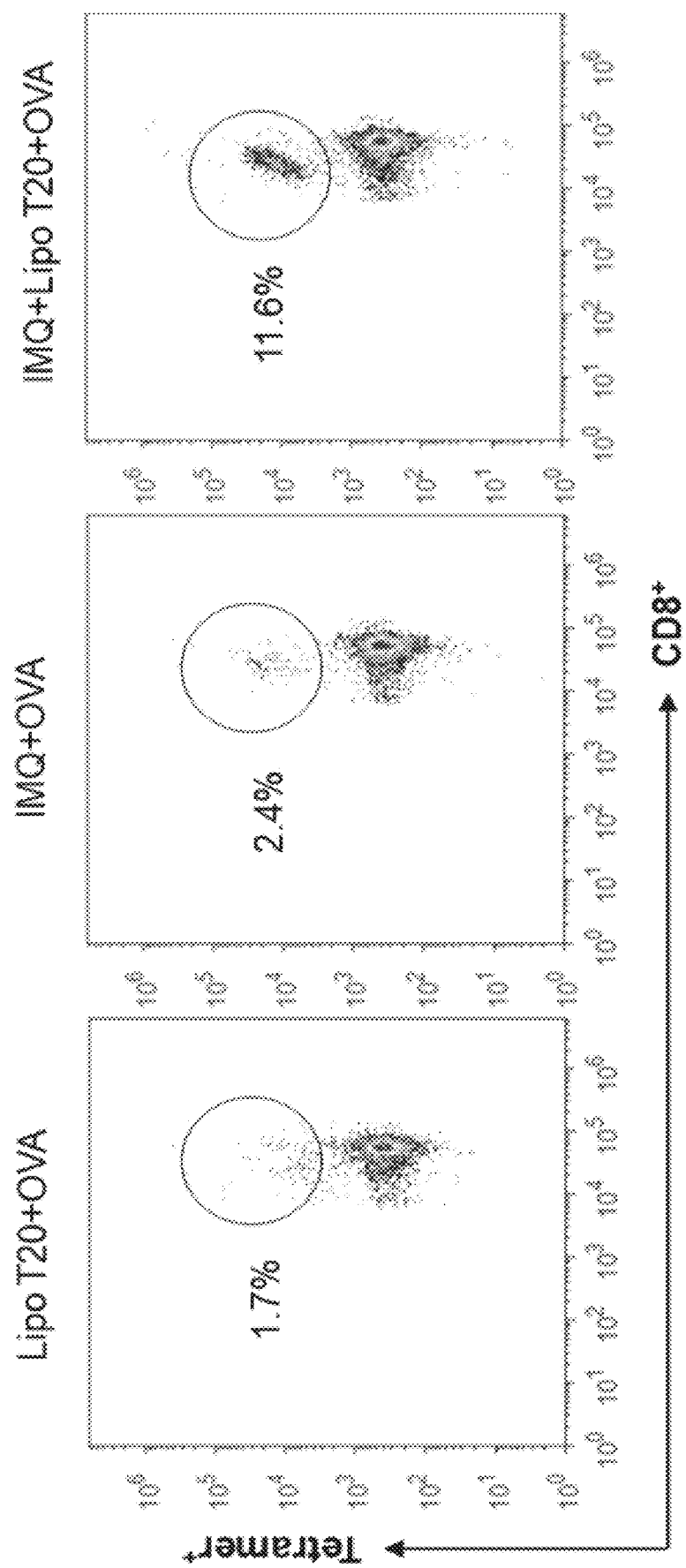

AMPHIPHILIC OLIGODEOXYNUCLEOTIDE CONJUGATES AS ADJUVANT ENHANCERS

CROSS-REFERENCE TO RELATED APPLICATION

This application claims priority to U.S. Provisional Application No. 62/810,844, filed Feb. 26, 2019, the entire contents of which are incorporated by reference herein as if fully set forth herein.

STATEMENT REGARDING FEDERALLY SPONSORED RESEARCH OR DEVELOPMENT

This invention was made with government support under Grant No. 1750607 awarded by the National Science Foundation. The government has certain rights in the invention.

FIELD OF THE DISCLOSURE

The current disclosure relates to adjuvant and other enhancers of immune stimulation, and more particularly to adjuvant enhancers including an amphiphilic oligonucleotide.

BACKGROUND OF THE DISCLOSURE

Vaccines remain the single most effective public health intervention ever developed, with millions of lives saved every year through the array of pediatric and adult vaccines administered globally. The first licensed vaccines were composed of inactivated or attenuated live microorganisms. Though these whole-microbe vaccines have been successful in preventing many infectious diseases, this approach is not applicable to some vaccine settings (e.g., therapeutic vaccines for cancer) or may not be safe (e.g., vaccines for HIV). Subunit vaccines that do not contain live components of the pathogens are safer, but are poorly immunogenic and require adjuvants to induce effective immune responses.

Adjuvants broadly defined are any substance added to a vaccine to augment (boost) immune response to the antigen. Adjuvants include diverse compounds including microbe-derived products that trigger conserved pathogen-recognition receptors; synthetic immunostimulatory molecules; and nanoparticles, microparticles, or oil/water emulsions. Adjuvants are important in vaccines, where they are often necessary to activate antigen presenting cells and facilitate the induction of cytotoxic T lymphocytes (CTLs) and antibodies.

Adjuvants boost vaccine immunity through different mechanisms. For example, adjuvants can function as delivery system, promote uptake and direct antigen presentation, or stimulate pathogens recognition receptors (PRRs). Molecules that can engage the Toll-like receptors (TLRs, one of the PPR families) are particularly powerful adjuvants which initiate innate and adaptive immune responses. However, attempts to develop new generation of adjuvants have been hindered by the fact that many adjuvants, although potent in vitro, lack of the physicochemical and pharmacokinetic properties that are critical in vivo.

Small molecular immune modifiers (IRMs) such as Imiquimod (R837) and Resiquimod (R848) stimulate TLR7 and/or TLR8, and are approved as monotherapeutic agents for human uses for external genital warts and certain skin cancers. IRMs are powerful adjuvants that enhance both antibody and cytotoxic T cell response. However, these IRMs have poor solubility, induce strong local and systemic inflammatory reactions, and are poorly tolerated. In fact, despite the potent in vitro immune stimulatory activities, R837 and R848 are presently limited to topical uses. Thus, there is an urgent and on-going need to develop advanced approaches to overcome these limitations of IRMs as vaccine adjuvants.

Current paradigms to enhance efficacy and safety of vaccine adjuvants are dominated by delivery systems to target immune cells while minimizing systemic exposure. However, it remains difficult to rationally design delivery formulations that meet all the requirements for vaccines. Possible stability, toxicological issues, complexity and cost greatly restrict their clinical application.

SUMMARY OF THE DISCLOSURE

Described herein is a novel molecular approach that amplifies the immunostimulatory effects of IRMs in vitro and in vivo. Certain non-stimulatory amphiphilic oligodeoxynucleotides (amph-oligos) are demonstrated to act as adjuvant enhancers (boosters), which significantly amplify the magnitude and function of IRMs in TLR stimulation. Addition of an amph-oligo to soluble IRMs greatly enhanced the NF-κB activation in both murine and human reporter cells, and induced 3-5-fold increases in cytokine production in primary immune cells. Importantly, co-administration of amph-oligos with low dose IRMs and protein antigen elicited 5-fold increases in antigen-specific T cells priming and antibody production in mice.

Thus, provided herein is a simple strategy to boost adjuvant efficacy for vaccine applications. This technology is believed to be broadly applicable for vaccines against infectious diseases and cancer, where efficacy and safety are needed.

Provided in a first embodiment is an amphiphilic oligonucleotide conjugate including: a lipophilic component; and directly or indirectly (e.g., through a linker) conjugated thereto an immunomodulating oligonucleotide that, if it were not conjugated to the lipophilic component, would suppress TLR7 and/or TLR8 stimulation. The lipophilic (amphiphilic) component may be conjugated to the oligonucleotide component at its 5' or 3' terminal end, or at a position that is not at a terminus of the oligonucleotide.

In examples of the amphiphilic oligonucleotide conjugate embodiments, the lipophilic component includes a phospholipid, a diacyl lipid, a fatty acid, a cholesterol, or a steroid. In some instances, the lipophilic component includes a linear, branched, or cyclic lipid 8-30 carbons in length. Specific example lipophilic components are described herein.

In embodiments of the amphiphilic oligonucleotide conjugates, the immunomodulating oligonucleotide includes an oligodeoxynucleotide (ODN); for instance, an ODN that includes 5-50 nucleotides, or in some instances includes 15-25 nucleotides. By way of example, the ODN in some conjugates includes a poly-oligo(dT) of 5-50 nucleotides (T5-T50), or a poly-oligo(dT) of 18-25 nucleotides (T18-T25).

Optionally, the oligonucleotide (or ODN) component of the conjugate includes a phosphorothioate bond or another modified (that is, non-naturally occurring) bond. Optionally, such non-naturally occurring bond provides one or more additional characteristics to the conjugate, such as increased stability.

In specific examples of the amphiphilic oligonucleotide conjugate, the immunomodulating oligonucleotide component includes the sequence of SEQ ID NO: 1, SEQ ID NO: 2, SEQ ID NO: 3, or SEQ ID NO: 4.

Optionally, the amphiphilic oligonucleotide conjugates provided herein include a linker between the lipophilic component and the immunomodulating oligonucleotide.

Also provided in another embodiment is the use of amphiphilic oligonucleotide conjugates described herein to improve efficacy of a vaccine. By way of example, improved efficacy in this context includes one or more of increased immunostimulation, increased TLR7 stimulation, increased NF-κB activation in reporter cells, increased cytokine production in primary immune cells, lower $EC_{50}$, reduced toxicity, increased antigen-specific CD8 T cell response, and increased humoral response. In examples of this use embodiment, the use occurs in vivo in the presence of albumin.

Yet another embodiment is an immunogenic composition including at least: an antigen; a TLR7- or TLR8-mediated adjuvant; and an amphiphilic oligonucleotide conjugate. Optionally, such immunogenic composition may further include at least one element of a delivery system.

In examples of the immunogenic composition, the antigen includes a viral antigen, a bacterial antigen, a parasite antigen, an allergen, an environmental antigen, or a cancer antigen. Optionally, the antigen includes a subunit antigen.

In specific examples of the immunogenic composition, the TLR7- or TLR8-mediated adjuvant includes a TLR7/TLR8 ligand, a single-stranded RNA, an oligoribonucleotide (ORN), a base analog (such as Loxoribine, CL075, CL097, CL264, CL307, or TLR8-506), or an imidazoquinolinamine (such as imiquimod (R837; IMQ), resiquimod (R848), or gardiquimod).

Examples of the immunogenic composition further include at least one additional adjuvant (that is, an adjuvant in addition to a first TLR7/TLR8-mediated adjuvant or TLR7/TLR8 ligand).

Another embodiment is an enhanced adjuvant composition including: an adjuvant (such as a TLR7/TLR8-mediated adjuvant) and at least one amphiphilic oligonucleotide conjugate in an amount sufficient to enhance an immune response to an antigen when the enhanced adjuvant composition is administered to a mammal.

Also provided is a method of enhancing TLR-mediated activation in a subject in need thereof, including administering to the subject a therapeutically effective amount of an amphiphilic oligonucleotide conjugate.

Yet another embodiment is a method of improving therapeutic efficacy of an imidazoquinolinamine, including administering the imidazoquinolinamine concurrently with an amphiphilic oligonucleotide conjugate. In specific examples of this embodiment, the imidazoquinolinamine is imiquimod (IMQ) or gardiquimod (GDQ). By way of example, improving therapeutic efficacy of an imidazoquinolinamine (or of IMQ) includes inducing a higher level of NF-κB stimulation and/or promoting the secretion of proinflammatory cytokines It is also understood that this disclosure encompasses amphiphilic oligonucleotide conjugates, compositions including an amphiphilic oligonucleotide conjugate, and methods of using an amphiphilic oligonucleotide conjugate essentially as described herein.

BRIEF DESCRIPTION OF THE DRAWINGS

(FIG. 1A) Molecular structures of imiquimod (IMQ; R837), Resiquimod (R848), Gardiquimod, and single-stranded DNA sequences of IRS 954 (SEQ ID NO: 1), lipo IRS 954 (SEQ ID NO: 6), and T20 (SEQ ID NO: 2). (FIG. 1B) Raw-Blue cells were stimulated with 2 μM IMQ alone or IMQ+1 μM IRS 954 or lipo IRS 954 for 24 h, NF-κB activation was quantified by measuring the SEAP levels in the supernatant. (FIG. 1C) Raw-Blue cells were stimulated with 2 μM IMQ alone or plus 1 μM T20 or lipo T20 for 24 h, NF-κB activation was quantified by measuring the T20 levels in the supernatant. (FIG. 1D) Raw-Blue cells were stimulated with 10 μg/ml Poly I:C, 2 μM IMQ and 100 nM CpG ODN 1826 alone, or plus 1 μM lipo T20 respectively for 24 h; NF-κB activation was quantified by measuring the SEAP levels in the supernatant. Data show the mean values ±SEM. *, $p<0.05$; , $p<0.01$; *, $p<0.001$; ****, $p<0.0001$; ns, not significant by one-way ANOVA with Bonferroni post-test.

FIGS. 2A-2D: (FIG. 2A) Raw-Blue cells were stimulated with 2 μM IMQ alone or plus 1 μM lipo T20 or lipo (EG)48 for 24 h. (FIG. 2B) Flow cytometry analysis of DC 2.4 cells treated with 1 μM of FAM-T20 or FAM-lipo T20 for 12 h or 24 h at 37° C. (FIG. 2C) Raw-Blue cells were stimulated with 2 μM IMQ alone or plus 1 μM lipo T20 or 5 μM T20 for 24 h. (FIG. 2D) Representative confocal images of DC 2.4 cells treated with 1 μM Cy5-labeled T20 and FAM-labeled lipo T20 simultaneously. Scale bar: 10 μm. Data show the mean values ±SEM. *, $p<0.05$; , $p<0.01$; *, $p<0.001$; ****, $p<0.0001$; ns, not significant by one-way ANOVA with Bonferroni post-test or unpaired Students' t-test.

(FIG. 4A) Flow cytometry analysis of DC 2.4 cells treated with endocytosis inhibitors for 30 min, followed by 1.5 h incubation with 1 μM FAM-labeled T20 or lipo T20 or 1 μM Alexa-647 BSA respectively, (FIG. 4B) Raw-Blue reporter cells were stimulated with 2 μM IMQ alone or in combination with 1 μM T20 or lipo T20 under FBS-free and normal culture conditions respectively for 24 h, (FIG. 4C) Flow cytometry analysis of Raw-Blue reporter cells which were cultured with complete or FBS-free medium separately for 24 h and then stained with Annexin V and PI for cell apoptosis assay, (FIG. 4D) Raw-Blue reporter cells were stimulated with 2 μM IMQ alone or in combination with 1 μM lipo T20 pre-complexed with BSA at 1:1 and 1:2 ratio respectively under FBS-free (O/F) condition for 24 h; Meanwhile, Raw-Blue reporter cells were stimulated with 2 μM IMQ alone or in combination with 1 μM lipo T20 under FBS-supplemented (W/F) condition for 24 h. Data show the mean values ±SEM. *, $p<0.05$; , $p<0.01$; *, $p<0.001$; ****, $p<0.0001$; ns, not significant by one-way ANOVA with Bonferroni post-test.

FIGS. 5A-5D: (FIG. 5A) Representative confocal images of Raw-Blue reporter cells treated with 1 μM FAM-labeled T20 or FAM-labeled lipo T20 under FBS-supplemented condition, or (FIG. 5B) under FBS-free condition, and then washed and stained with 50 nM LysoTracker Red following manufacturer's instructions. Scale bar: 10 μm. (FIG. 5C) Raw-Blue cells were stimulated with 2 μM IMQ alone or in combination with 1 µM disulfide bond-linked T20 or lipo T20 or BSA-T20 conjugate under FBS-supplemented condition, (FIG. 5D) under FBS-free condition, for 24 h. Data show the mean values ±SEM. *, p<0.05; , p<0.01; *, p<0.001; ****, p<0.0001; ns, not significant by one-way ANOVA with Bonferroni post-test.

FIGS. 6A-6G: (FIG. 6A) Structure of C18 diacyl lipid conjugated poly-oligo(dT) and C14 diacyl lipid conjugated T20, (FIG. 6B) Raw-Blue reporter cells were stimulated with 2 µM IMQ alone or with 1 µM lipo T10, lipo T20, lipo T25 and lipo T50 for 24 h, (FIG. 6C) Raw-Blue reporter cells were stimulated with 2 µM IMQ alone or in combination with 1 µM C14 diacyl lipid-modified T20 or C18 diacyl lipid-modified T20 for 24 h, (FIG. 6D) Raw-Blue cells were stimulated with 2 µM IMQ alone or in combination with 1 µM lipo T10, lipo T20, lipo T25 and lipo T50 for 24 h, (FIG. 6E) Structure of 3'- and 5'-modified Cholesterol T20, (FIG. 6F) HEK mTLR7 reporter cells were stimulated with 2 µM IMQ alone or in combination with 1 µM 3'- and 5'-modified Cholesterol T20 for 24 h, (FIG. 6G) HEK mTLR8 reporter cells were stimulated with 2 µM R848 alone or in combination with 1 µM 3'- and 5'-modified Cholesterol T20 for 24 h. Data show the mean values ±SEM. *, p<0.05; , p<0.01; *, p<0.001; ****, p<0.0001; ns, not significant by one-way ANOVA with Bonferroni post-test.

(FIGS. 7D-7F) HEK mouse TLR8 (mTLR8) reporter cells were stimulated with IMQ, CL075, R848 respectively at indicated concentrations alone or in combination with 1 µM T20 or lipo T20 for 24 h, NF-κB activation was quantified by measuring the SEAP levels in the supernatant. (FIGS. 7G-7I) Raw-Blue reporter cells were stimulated with IMQ, CL075, R848 respectively at indicated concentrations alone or in combination with 1 µM T20 or lipo T20 for 24 h, NF-κB activation was quantified by measuring the SEAP levels in the supernatant.

(FIG. 8A) HEK human TLR7 (hTLR7) reporter cells were stimulated with 2 µM IMQ alone or in combination with 1 µM T20 or lipo T20, 1 µM IRS 954 or lipo IRS 954, 1 µM ODN 2087 or lipo ODN 2087 respectively for 24 h, NF-κB activation was quantified by measuring the SEAP levels in the supernatant. (FIG. 8B) HEK hTLR7 reporter cells were stimulated with IMQ at indicated concentrations alone or in combination with 1 µM T20 or lipo T20 for 24 h, NF-κB activation was quantified by measuring the SEAP levels in the supernatant. (FIG. 8C) HEK hTLR8 reporter cells were stimulated with 1 µg/ml TLR8-506 alone or in combination with 1 µM T20 or lipo T20, 1 µM ODN 2087 or lipo ODN 2087 respectively for 24 h, NF-κB activation was quantified by measuring the SEAP levels in the supernatant. (FIG. 8D) HEK hTLR8 reporter cells were stimulated with TLR8-506 at indicated concentrations alone or in combination with 1 µM T20 or lipo T20 for 24 h, NF-κB activation was quantified by measuring the SEAP levels in the supernatant. Data show the mean values ±SEM. *, p<0.05; , p<0.01; *, p<0.001; ****, p<0.0001; ns, not significant by one-way ANOVA with Bonferroni post-test.

(FIG. 9E, 9F) human PBMC were incubated with CL264, or TLR8-506 in the presence of T20 or lipo T20 for 24 h, IFN-α and IL-12p40 were quantified in the supernatant by ELISA. (FIG. 9G) Representative flow cytometry plots of pDC enriched from human peripheral blood mononuclear cells (PBMC), (FIG. 9H) human pDC cells were stimulated with 2 µM IMQ alone or in combination with 1 µM T20 or lipo T20 for 24 h, and IFN-α secreted by pDC cells was determined by ELISA, (FIG. 9I) Human PBMC cells were stimulated with 60 nM TLR8-506 alone or in combination with 1 µM T20 or lipo T20 for 24 h, and TNF-α secreted by PBMC cells was determined by ELISA. Data show the mean values ±SEM. *, p<0.05; , p<0.01; *, p<0.001; ****, p<0.0001; ns, not significant by one-way ANOVA with Bonferroni post-test.

FIG. 10A-10E. On day 0 and day 14, C57BL/6 mice were immunized with 50 µg Ovalbumin (OVA) and 15 µg IMQ mixed with or without 6.2 nmol lipo T20 dissolved in PBS. Blood samples were collected on day 20. (FIG. 10A) Representative flow cytometry plots of H-2K$^b$/SIINFEKL tetramer frequencies of CD$^8$ cells. (FIG. 10B) Quantification of H-2K$^b$/SIINFEKL tetramer staining of CD$^8$ cells. (FIG. 10C) Quantification of IFN-γ-secreting CD$^{8+}$ T cell determined by intracellular cytokine staining. (FIG. 10D) Quantification of TNF-α-secreting CD$^{8+}$ T cell determined by intracellular cytokine staining. (FIG. 10E) On day 20, serum samples were collected and assayed by ELISA for anti-OVA IgG production. Data show the mean values ±SEM. *, p<0.05; , p<0.01; *, p<0.001; ****, p<0.0001; ns, not significant by one-way ANOVA with Bonferroni post-test.

(FIG. 11A) Representative structure of lymph node-targeting amphiphilic IRM with cleavable linker. (FIG. 11B) Representative structure of an amphiphilic oligodeoxynucleotide (Liu et al., Nature 507:519-522, 2014; U.S. Pat. Nos. 9,107,904 and 10,029,016) useful as adjuvant enhancer for IRM.

REFERENCE TO THE SEQUENCE LISTING

Figure 1A:
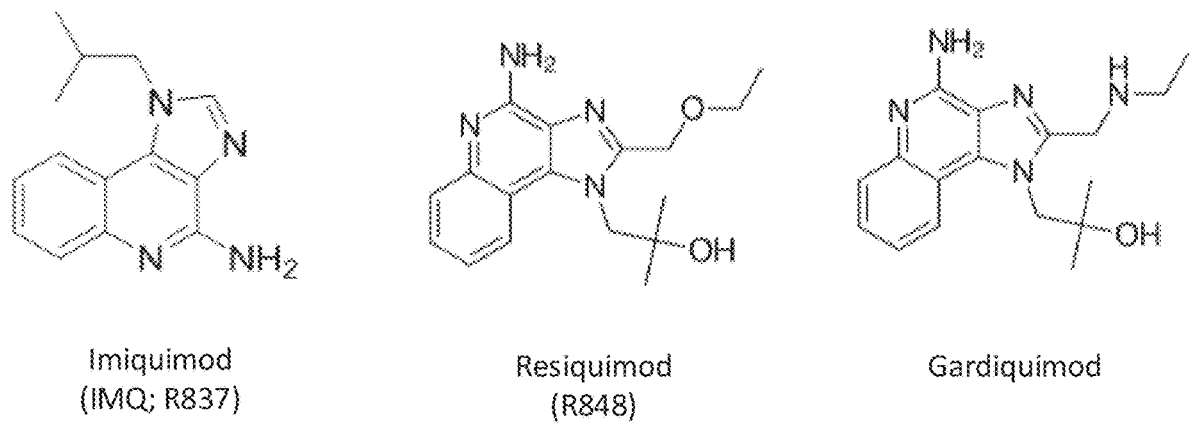
FIGS. 1A-1D.
Figure 1A:
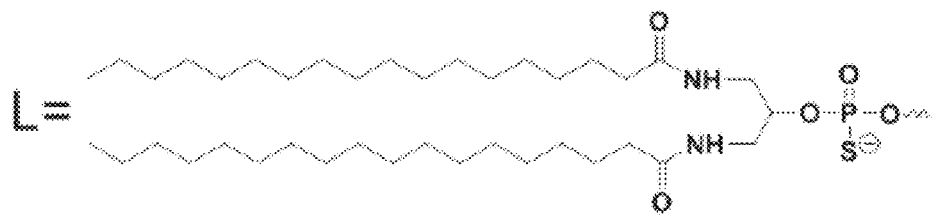

The nucleic acid and/or amino acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate. A computer readable text file, entitled "DN28W5311.txt (Sequence_Listing.txt)" created on or about Feb. 12, 2020, with a file size of 8 KB, contains the Sequence Listing for this application and is hereby incorporated by reference in its entirety. In the accompanying Sequence Listing:

SEQ ID NO: 1 is the nucleotide sequence of IRS 954 (5'-TGCTCCTGGAGGGGTTGT-3').

SEQ ID NO: 2 is the nucleotide sequence of T20 (5'-TTTTTTTTTTTTTTTTTTTT-3').

SEQ ID NO: 3 is the nucleotide sequence of ODN 2087 (5'-TCCTGAGCTTGAAGT-3').

SEQ ID NO: 4 is the nucleotide sequence of CpG ODN 1826 (5'-TCCATGACGTTCCTGACGTT-3').

SEQ ID NO: 5 is the amino acid sequence of Ovalbumin peptide OVA257-264 (SIINFEKL), which is recognized by Antibody H-2Kb.

SEQ ID NO: 6 is the nucleotide sequence of lipo IRS 954 (5'-L-TGCTCCTGGAGGGGTTGT-3').

DETAILED DESCRIPTION

Subunit vaccines must be combined with adjuvants in order to be effective. However, the use of adjuvants in vaccines is like a double-edged sword: they enhance the immunogenicity of subunit antigens, but also non-specifically activate the immune system to induced toxicity and side effects. Thus there is a need to improve the efficacy of adjuvants in vaccines.

Provided herein are adjuvant enhancers that can simply be added to current vaccine preparations without further formulation. The enhanced immune response provide by these adjuvant enhancers (boosters) is believed to also allow for dose sparing of both antigens and adjuvants, thereby reducing their toxicity and side effects.

The technology disclosed herein can boost the immunostimulatory effect of certain Toll-Like receptor (TLR) ligands without compromising the dose, formulation, and administration of current subunit vaccines. Thus described, adjuvant enhancing amphiphilic oligonucleotide conjugates are believed to be broadly applicable for use with any vaccines that employ IRMs as adjuvants.

Prior approaches to enhance vaccine efficacy focused on the design of delivery systems that target the immune cells while minimizing the systemic exposure. In contract, the herein described amphiphilic oligonucleotides are capable of targeting antigen presenting cells in the lymph nodes through 'albumin-hitchhiking', and can be combined with current delivery approaches (including, for instance, those taught in U.S. Patent Publication No. 2019/0015522 and EP 2833918B1).

Adjuvant Enhancing Amphiphilic Oligodeoxynucleotides (Amph-Oligos)

Described herein is the development of lipid-modified oligonucleotide-based TLR7/8 inhibitors that improve the potency and efficacy of TLR7/8 ligands, including in the presence of albumin. These lipo ODNs (amph-oligos) tolerate a wide range of sequences, but the structurally-optimized lipo poly (dT) (20-25 nucleotides) showed maximal enhancing effects. Lipo T20 was applicable to human cells and was able to enhance human TLR7- and TLR8-mediated NF-κB stimulation. However, lipo T20 still conserved the immunosuppressive capability of reducing TLR7-mediated production of IFN-α in both murine and human cells. Lipo T20 is shown to be a powerful adjuvant enhancer in enhancing the immune responses to molecular vaccines, as lacing a subunit vaccine formulation with lipo T20 led to markedly improved cellular and humoral responses in mice. Thus, the amphiphilic oligonucleotide conjugates (amph-oligos) provide herein are believed to be broadly applicable as adjuvant enhancers useful in vaccines, including for instance in current existing vaccines where both efficacy and safety are needed.

The adjuvant enhancing amph-oligos include at least (1) an immunomodulating oligonucleotide that would suppress TLR7 stimulation if it were unmodified (that is, if it were not conjugated to a lipophilic domain), and (2) a lipophilic domain, conjugated directly or indirectly (for instance, via a linker) to the oligonucleotide. The Example and Figures provided herewith describe variations of specific embodiments of adjuvant enhancing amph oligos, but it will be understood that additional variations are contemplated. The following sections provide description of additional variations and options.

Immunomodulating Oligonucleotide

The oligonucleotide component of amph-oligos can bear a wide range of sequences, lengths, and structures. In general, the oligonucleotide component is an immunomodulating oligonucleotide that, if it were not part of the conjugate (that is, if it were not modified by the addition of a lipophilic moiety), would suppress TLR7 stimulation. See, for instance, EP1928500A2 (Modulation of TLR-Mediated Immune Responses Using Adaptor Oligonucleotides); U.S. Pat. No. 9,347,064 (Methods of treatment using TLR7 and/or TLR9 inhibitors); U.S. Patent Publication No. 2013/0156814A1 (Methods of treatment using TLR7 and/or TLR9 inhibitors); WO 2006/063072 (Immunomodulatory compositions, combinations and methods); and AU 2006/304205C1 (Immune regulatory oligonucleotide (IRO) compounds to modulate toll-like receptor based immune response).

In specific embodiment, the oligo component includes an oligodeoxynucleotide (ODN). Specific examples of oligo component are poly-oligo(dT)s (that is, strings of thymine nucleotides), such as a poly-oligo(dT) of 5-50 nucleotides (that is, T5-T50), for instance oligos of 8, 10, 12, 15, 18, 19, 20, 21, 22, 23, 24, 25, 28, 30, 35, 40, 45 or 50 thymine nucleotides. Additional specific example oligos include those shown in SEQ ID NO: 1-4.

Methods of making both natural and modified (non-naturally occurring) oligonucleotides are well known in the art. Oligonucleotides are connected by an internucleotide bond that refers to a chemical linkage between two nucleoside moieties. Modifications to the phosphate backbone of DNA or RNA oligonucleotides may increase the binding affinity or stability of oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak et al., *Organic Chem.*, 52:4202, 1987), and uncharged morpholino-based polymers having achiral intersubunit linkages (see, for instance, U.S. Pat. No. 5,034,506). Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch et al., *Chem. Biol.*, 8(1):1-7, 2001). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides include peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571 and 5,786, 571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the oligonucleotide is single-stranded DNA, single-stranded RNA, or double-stranded RNA.

Lipophilic Component

The conjugates disclosed herein typically include a lipophilic (hydrophobic) component, such as a lipid. The lipid can be linear, branched, or cyclic. The lipid is preferably at least 8-30 carbons in length.

In example embodiments, the adjuvant-enhancing activity of the provided conjugates rely, at least in part, on the ability of the conjugate to associate with albumin (for instance, in the blood of the subject). Therefore, representative conjugates include a lipid that can bind to (associate with) albumin under physiological conditions. Lipids suitable for use in the herein provided conjugates can be selected based on the ability of the lipid, or an amphiphilic oligonucleotide conjugate including the lipid, to bind to albumin. Suitable methods for testing the ability of the lipid or amphiphilic oligonucleotide conjugate to bind to albumin are known in the art, including methods discussed in the Example below.

Examples of preferred lipids for use in amphiphilic oligonucleotide conjugates include, but are not limited to fatty acids with aliphatic tails of 8-30 carbons including, but not limited to, linear unsaturated and saturated fatty acids, branched saturated and unsaturated fatty acids, and fatty acids derivatives, such as fatty acid esters, fatty acid amides, and fatty acid thioesters, diacyl lipids, Cholesterol, Cholesterol derivatives, and steroid acids such as bile acids; Lipid A or combinations thereof.

In some embodiments, the lipid is a diacyl lipid or two-tailed lipid. In some embodiments, the tails in the diacyl lipid contain from about 8 to about 30 carbons and can be saturated, unsaturated, or combinations thereof. The tails can be coupled to the head group via ester bond linkages, amide bond linkages, thioester bond linkages, disulfide linkages, maleimide linkages, hydrazone linkages, enzyme-activatable linkages, or combinations of two or more thereof. In a particular embodiment, the diacyl lipids are phosphate lipids, glycolipids, sphingolipids, or combinations thereof.

Preferably, lymph node-targeting conjugates include a lipid that is 8 or more carbon units in length. It is believed that increasing the number of lipid units can reduce insertion of the lipid into plasma membrane of cells, allowing the amphiphilic oligonucleotide conjugate to remain free to bind albumin and traffic to the lymph node.

For example, the lipid can be a diacyl lipid composed of two C18 hydrocarbon tails.

In some embodiments, the lipid for use in preparing amphiphilic oligonucleotide conjugates is not a single chain hydrocarbon (e.g., C18); for instance, non-linear lipids include cholesterol, bile acids, and steroids. Cholesterol conjugation has been explored to enhance the immunomodulation of molecular adjuvants such as CpG and immunogenicity of peptides, but cholesterol conjugates, which associates well with lipoproteins but poorly with albumin, show poor lymph node targeting and low immunogenicity in vaccines compared to optimal albumin-binding conjugates.

For additional discussion of lipid-modification of oligonucleotides, including representative methods, see for instance, Irby et al. (*Mol Pharm* 14(5):1325-1338, 2017); Winkler (*Ther Deliv.* 4(7):791-809, 2013); and US Patent Publications 2007/0275047 and 2019/0015522.

Optional Linker

The hydrophobic/lipophilic component and the immune-modulating oligonucleotide component are covalently linked (conjugated). The covalent bond may be a non-cleavable linkage or a cleavable linkage. The non-cleavable linkage can include an amide bond or phosphate bond, and the cleavable linkage can include a disulfide bond, acid-cleavable linkage, ester bond, anhydride bond, biodegradable bond, or enzyme-cleavable linkage. Optionally, a linker may be included between the lipophilic component and the oligonucleotide component.

Ethylene Glycol Linkers:

A linker in some embodiments is one or more ethylene glycol (EG) units, for instance two or more EG units (i.e., polyethylene glycol (PEG)). For example, in some embodiments, a lipophilic oligonucleotide conjugate includes an immunostimulatory (immune-modulating) oligonucleotide component and a hydrophobic/lipophilic component linked by a polyethylene glycol (PEG) molecule or a derivative or analog thereof.

The precise number of EG units depends on the lipid and the cargo, however, typically, a linker can have between about 1 and about 100, between about 20 and about 80, between about 30 and about 70, or between about 40 and about 60 EG units. In some embodiments, the linker has between about 45 and 55 EG, units. For example, the linker in some instances has 48 EG units. See, for instance, Kozlovskaya et al. (Biomedicine, DOI:10.5772/33951, 2012)

Oligonucleotide Linkers:

By way of further example, the linker may itself be an oligonucleotide. A linker oligonucleotide can have any sequence, for example, the sequence of the oligonucleotide can be a random sequence, or a sequence specifically chosen for its molecular or biochemical properties (e.g., highly polar). In some embodiments, the linker includes one or more series of consecutive adenine (A), cytosine (C), guanine (G), thymine (T), uracil (U), or analog thereof. In some embodiments, the linker consists of a series of consecutive adenine (A), cytosine (C), guanine (G), thymine (T), uracil (U), or analog thereof.

In one embodiment, the linker is one or more guanines, for example between 1-10 guanines. It has been discovered that altering the number of guanines between a domain such as a CpG oligonucleotide, and a lipid tail controls micelle stability in the presence of serum proteins. Therefore, the number of guanines in the linker can be selected based on the desired affinity of the conjugate for serum proteins such as albumin. In various embodiments, the linker in an adjuvant enhancing conjugate can include 0, 1, or 2 guanines.

Formulations

Pharmaceutical Compositions:

Pharmaceutical compositions including amphiphilic oligonucleotide conjugates are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the nanolipogels to the immediate area of the implant.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

Formulations for Parenteral Administration:

In a preferred embodiment the amphiphilic oligonucleotide conjugates are administered in an aqueous solution, by parenteral injection. In some embodiments, the composition includes albumin, or other serum proteins.

The formulation can be in the form of a suspension or emulsion. In general, pharmaceutical compositions are provided including an effective amount of the conjugate and optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN™ 20, TWEEN™ 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

Formulations for Topical and/or Mucosal Administration:

The amphiphilic oligonucleotide conjugates can be applied topically. Topical administration can include application to the lungs (pulmonary), nasal, oral (sublingual, buccal), vaginal, or rectal mucosa. In some cases, the conjugates may be transcytosed on albumin across mucosal barriers Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent™ nebulizer (Mallinckrodt Inc., St. Louis, Mo.); the Acorn™ II nebulizer (Marquest Medical Products, Englewood, Colo.); the Ventolin™ metered dose inhaler (Glaxo Inc., Research Triangle Park, N.C.); and the Spinhaler™ powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges.

Transdermal formulations may also be prepared. These will typically be ointments, lotions, sprays, or patches, all of which can be prepared using standard technology. Transdermal formulations can include penetration enhancers.

Immunogenic Compositions:

The amphiphilic oligonucleotide conjugates disclosed herein can be used in immunogenic compositions or as components in vaccines. An immunogenic composition can include an amphiphilic oligonucleotide conjugate that is an adjuvant enhancer such as an immunostimulatory oligonucleotide-lipid conjugate. Typically, immunogenic compositions disclosed herein include at least one amphiphilic oligonucleotide as well as an adjuvant, an antigen, or a combination thereof. The combination of an adjuvant and an antigen can be referred to as a vaccine. The phrase "subunit vaccine" can refer to a vaccine that does not contain a whole live or killed pathogen, but only a subunit (e.g., a single protein or protein fragment) of the pathogen (or more generally, target against which an immune response is to be mounted) that stimulates an immune response against the target. When administered to a subject "in combination", the adjuvant and antigen can be administered in separate pharmaceutical compositions, or they can be administered together in the same pharmaceutical composition.

Antigens

Optionally, an immunogenic composting can include (or be co-administered with) one or more antigens against which it is desired to mount an immune response. Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell, and can be a whole cell or immunogenic component thereof, e.g., cell wall components or molecular components thereof.

Suitable antigens are known in the art and are available from commercial government and scientific sources. In one embodiment, the antigens are whole inactivated or attenuated organisms. These organisms may be infectious organisms, such as viruses, parasites and bacteria. These organisms may also be tumor cells. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids. Exemplary antigens are provided below.

Viral Antigens:

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomegalovirus, Epstein-Barr, rotavirus, rhinovirus, adenovirus, coxsackieviruses, equine encephalitis, Japanese encephalitis, yellow fever, Rift Valley fever, and lymphocytic choriomeningitis.

Bacterial Antigens: Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio,* and *Yersinia.*

Parasite Antigens: Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.* These include Sporozoan antigens, *Plasmodium* antigens, such as all or part of a Circumsporozoite protein, a Sporozoite surface protein, a liver stage antigen, an apical membrane associated protein, or a Merozoite surface protein.

Allergens and Environmental Antigens:

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including birch (*Betula*), alder (*Alnus*), hazel (*Corylus*), hornbeam (*Carpinus*) and olive (*Olea*), cedar (*Cryptomeriaand Juniperus*), Plane tree (*Platanus*), the order of Poales including e.g., grasses of the genera *Lolium, Phleum, Poa, Cynodon, Dactylis, Holcus, Phalaris, Secale,* and *Sorghum,* the orders of Asterales and Urticales including i.a. herbs of the genera *Ambrosia, Artemisia,* and *Parietaria.* Other allergen antigens that may be used include allergens from house dust mites of the genus *Dermatophagoides* and *Euroglyphus,* storage mite e.g. Lepidoglyphys, Glycyphagus and Tyrophagus, those from cockroaches, midges and fleas e.g. *Blatella, Periplaneta, Chironomus* and *Ctenocepphalides,* those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium.*

Cancer Antigens:

A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2.

Adjuvants

Embodiments of the amphiphilic oligonucleotide conjugates described herein enhance biological activity of adjuvant(s) that act through TLR7 and/or TLR8. Thus, contemplated herein are compositions or treatment regimens that employ both an amphiphilic oligonucleotide conjugate and a TLR7/TLR8 adjuvant. Examples of such compositions are immunogenic compositions that include an amphiphilic oligonucleotide conjugate, an antigen, and an adjuvant that acts through TLR7 and/or TLR8. Adjuvants that act through TLR7 and/or TLR8 include single-stranded RNA, oligoribonucleotides (ORN), base analogs (such as Loxoribine, CL075, CL097, CL264, CL307, TLR8-506), synthetic low molecular weight compounds such as imidazoquinolinamines (e.g., imiquimod (R-837), resiquimod (R-848), or gardiquimod (GDQ)). See also U.S. Patent Publication No. 2019/0023687 (TLR7/8 Antagonists and Uses Thereof).

The compositions (including immunogenic compositions) may optionally contain one or additional adjuvant(s), beyond the TLR7/8-mediated ligand/adjuvant. Such additional adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene (PCPP polymer; Virus Research Institute, USA), Flt3 ligand, *Leishmania* elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic). Adjuvants are well known, including their use to enhance immunogenicity of sub-unit vaccines; see, for instance: Vogel, *Clin Infect Dis.* 30(Suppl 3):S266-S270, 2000; Kurella et al., *Indian J Clin Biochem* 15(Suppl 1):83-100, 2000; Christensen, *Hum Vaccin Immunother* 12(10):2709-2711, 2016.

Adjuvants may be TLR ligands, such as those discussed herein. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

The adjuvant can also be oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminum salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinoline compounds; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-γ), macrophage colony stimulating factor, and tumor necrosis factor.

Delivery Vehicle

Optionally, immunogenic compositions or vaccines can include a delivery vehicle. Myriad delivery vehicles and delivery vehicle systems are known in the art and more are continually being developed. By way of non-limiting example, the following references teach and/or review various delivery systems or vehicles for enhancing vaccine or immunogenic composition delivery: U.S. Patent Publication 2019/0015522A1 (delivery mediated by albumin binding, which enables trafficking to the lymph nodes); Hosseinzadeh & Bolhassani, *Curr Drug Deliv.* 12(4):360-368, 2015 (reviewing several vaccine delivery systems developed to generate immunomodulatory effects); Midoux & Pichon, *Expert Rev Vaccines.* 14(2):221-234, 2015 (lipid-based nucleic acid vaccine delivery systems); Schwendener, *Ther Adv Vaccines.* 2(6):159-182, 2014 (liposomes as vaccine delivery systems); Silva et al., *Hum Vaccin Immunother.* 12(4):1056-1069, 2016 (reviewing poly(lactic-co-glycolic acid) (PLGA) particle formulations for subunit vaccine delivery); Allahyari & Mohit, *Hum Vaccin Immunother.* 12(3):806-828, 2016 (vaccine deliver system based on PLGA particles); Bobbala & Hook, *Pharm Res.* 33(9):2078-2097, 2016 (reviewing formulations and delivery strategies for subunit vaccines); Trimaille & Verrier, *Vaccines (Basel),* 3(4):803-813, 2015 (reviewing micelle-based adjuvants as in subunit vaccine delivery); Asadi et al., *Artif Cells Nanomed Biotechnol.* 45(1):18-23, 2016 (reviewing delivery systems for cancer immunotherapy); Zamani et al., *J Cell Physiol.* 233(7):5189-5199, 2018 (reviewing use of nanoliposomes in delivery of cancer immunotherapy); Nakahasi-Ouchida et al., *Expert Rev Vaccines.* 16(12):1231-1240, 2017 (nanogel-based nasal vaccine delivery system); Shakya et al., *J Control Release.* 240:394-413, 2016 (mucosal vaccine delivery); Issue 10(9), 2014 of *J. Biomed Nanotechnology* (special issue focused on nanomedicine, drug delivery, and vaccine development); and Wang et al., *Drug Deliv.* 25(1):1319-1327, 2018 (nanoparticle delivery systems for tumor peptide vaccines).

Combination Therapies

In some embodiments, the conjugates are administered in combination with one or more additional therapeutic agents. The agents can be administered in the same pharmaceutical composition as the conjugates or the conjugates and the additional therapeutic agent can be administered in separate pharmaceutical compositions. Concurrent administration does not require that the compositions are mixed with each other, or that they are administered exactly at the same time; the term contemplates overlapping administration as well as sequential administration. Thus, "co-administration of", "concurrent administration of", or administration "in conjunction with" an amphiphilic oligonucleotide conjugate, for instance with an adjuvant, an antigen, or another therapeutic agent, does not require that the conjugate and the adjuvant, or the conjugate and the antigen, or all three, or the conjugate and a second therapeutic compound, are all mixed in a single composition.

In some embodiments, the conjugates are administered in combination with a conventional therapeutic agent used for treatment of the disease or condition being treated. Conventional therapeutics agents are known in the art and can be determined by one of skill in the art based on the disease or disorder to be treated. For example, if the disease or condition is cancer, the conjugates can be co-administered with a chemotherapeutic drug; or if the disease or condition is a bacterial infection, the conjugates can be co-administered with an antibiotic.

Methods of Use

Methods of Increasing an Immune Response:

Amphiphilic oligonucleotide conjugates can be administered in an effective amount, for instance in conjunction with an adjuvant, to induce, increase or enhance an immune response. The "immune response" refers to responses that induce, increase, or perpetuate the activation or efficiency of innate or adaptive immunity. The conjugates can be delivered parenterally (by subcutaneous, intradermal, or intramuscular injection) through the lymphatics, or by systemic administration through the circulatory system. It is noted that lymph nodes can filter albumin-bound conjugates. Therefore, in some embodiments parenteral administration does not result in systemic distribution, as the conjugates may be preferentially filtered by the closest lymph node(s). This tendency also reduces systemic toxicity such as swelling of the spleen.

Accordingly, in some embodiments, the conjugates are administered at a site adjacent to or leading to one or more lymph nodes which are close to the site in need of an immune response (i.e., close to a tumor or site of infection). In some embodiments, the conjugates are administered in multiple doses at various locations throughout the body. The conjugates can also be administered directly to a site in need of an immune response (e.g., a tumor or site of infection).

The immune response can be induced, increased, or enhanced by the amphiphilic oligonucleotide conjugate with an adjuvant compared to a control, for example an immune response in a subject induced, increased, or enhanced by the adjuvant alone, or the adjuvant along with the antigen (that is, simply without the conjugate).

The amphiphilic oligonucleotide conjugates can be used, for example, to induce or enhance an immune response, when administering an antigen alone, or the antigen with an adjuvant, or the antigen with an adjuvant and in combination with an alternative delivery system, is ineffectual. The amphiphilic oligonucleotide conjugates can also be used to enhance or improve the immune response compared to administering antigen alone or with adjuvant. In some embodiments, the amphiphilic oligonucleotide conjugates may reduce the dosage required to induce, increase, or enhance an immune response; and/or reduce the time needed for the immune system to respond following administration; and/or reduce side effects.

Amphiphilic oligonucleotide conjugates may be administered as part of prophylactic vaccines or immunogenic compositions that confer resistance in a subject to subsequent exposure to infectious agents, or as part of therapeutic vaccines, which can be used to initiate or enhance a subject's immune response to a pre-existing antigen, such as a viral antigen in a subject infected with a virus or with cancer.

The desired outcome of a prophylactic or therapeutic immune response may vary according to the disease or condition to be treated, or according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

The amphiphilic oligonucleotide conjugates induce an improved effector cell response such as a CD4 T-cell immune response, against at least one of the component antigen(s) or antigenic compositions compared to the effector cell response obtained with the corresponding composition without the amphiphilic oligonucleotide conjugate. The term "improved effector cell response" refers to a higher effector cell response such as a CD8 or CD4 response obtained in a human patient after administration of the vaccine composition than that obtained after administration of the same composition without an amphiphilic oligonucleotide conjugate.

The improved effector cell response can be obtained in an immunologically unprimed patient, i.e. a patient who is seronegative to the antigen. This seronegativity may be the result of the patient having never faced the antigen (so-called "naive" patient) or, alternatively, having failed to respond to the antigen once encountered. In some embodiments, the improved effector cell response is obtained in an immunocompromised subject.

The improved effector cell response can be assessed by measuring the number of cells producing any of the following cytokines: (1) cells producing at least two different cytokines (CD40L, IL-2, IFN-gamma, TNF-alpha); (2) cells producing at least CD40L and another cytokine (IL-2, TNF-alpha, IFN-gamma); (3) cells producing at least IL-2 and another cytokine (CD40L, TNF-alpha, IFN-gamma); (4) cells producing at least IFN-gamma and another cytokine (IL-2, TNF-alpha, CD40L); (5) and cells producing at least TNF-alpha and another cytokine (IL-2, CD40L, IFN-gamma).

An improved effector cell response is present when cells producing any of the above cytokines will be in a higher amount following administration of the vaccine composition compared to control as discussed above.

In a preferred embodiment, the composition increases the number of T cells producing IFN-gamma, TNF-alpha, or a combination thereof, or increases the production of IFN-gamma, TNF-alpha, or a combination thereof in the existing T cells.

In some embodiments, the administration of the immunogenic composition alternatively or additionally induces an improved B-memory cell response in patients administered amphiphilic oligonucleotide conjugates compared to a control. An improved B-memory cell response is intended to mean an increased frequency of peripheral blood B lymphocytes capable of differentiation into antibody-secreting plasma cells upon antigen encounter as measured by stimulation of in vitro differentiation.

In a still another embodiment, the immunogenic composition increases the primary immune response as well as the CD8 response. The administration of the amphiphilic oligonucleotide conjugates induces an improved CD4 T-cell, or CD8 T-cell immune response against a specific antigen compared to a control. This method may allow for inducing a CD4 T cell response which is more persistent in time. Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

Diseases to be Treated or Reduced/Prevented

Cancer:

The disclosed amphiphilic oligonucleotide conjugates are useful, in conjunction with an adjuvant, for stimulating or enhancing an immune response in host for treating cancer. The types of cancer that may be treated with the provided compositions and methods include, but are not limited to, the following: bladder, brain, breast, cervical, colo-rectal, esophageal, kidney, liver, lung, nasopharyngeal, pancreatic, prostate, skin, stomach, uterine, ovarian, testicular, and hematologic.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The conjugates can be administered in as an immunogenic composition or as part of vaccine, such as prophylactic vaccines, or therapeutic vaccines, which can be used to initiate or enhance a subject's immune response to a pre-existing antigen, such as a tumor antigen in a subject with cancer.

The desired outcome of a prophylactic or therapeutic immune response may vary according to the disease, according to principles well known in the art. Similarly, immune responses against cancer, may alleviate symptoms, or may be one facet in an overall therapeutic intervention against a disease. For example, administration of the amphiphilic oligonucleotide conjugates may reduce tumor size, or slow tumor growth compared to a control. The stimulation of an immune response against a cancer may be coupled with surgical, chemotherapeutic, radiologic, hormonal and other immunologic approaches in order to affect treatment.

Infectious Diseases:

In additional embodiments, the amphiphilic oligonucleotide conjugates are useful for treating acute or chronic infectious diseases. Because viral infections are cleared primarily by T-cells, an increase in T-cell activity is therapeutically useful in situations where more rapid or thorough clearance of an infective viral agent would be beneficial to an animal or human subject. Thus, the amphiphilic oligonucleotide conjugates can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the amphiphilic oligonucleotide conjugates can be administered topically to treat viral skin diseases such as herpes lesions or shingles, or genital warts. The amphiphilic oligonucleotide conjugates can also be administered to treat systemic viral diseases, including, but not limited to, AIDS, influenza, the common cold, or encephalitis.

Representative infections that can be treated, include but are not limited to infections caused by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus* influenza type B (HIB), *Histoplasma, Hyphomicrobium, Legionella, Leishmania, Leptospirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia rickestii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis,* and *Schistosoma mansoni.*

In some embodiment, the type of disease to be treated or prevented is a chronic infectious disease caused by a bacterium, virus, protozoan, helminth, or other microbial pathogen that enters intracellularly and is attacked, e.g., by cytotoxic T lymphocytes.

In a preferred embodiment, infections to be treated are chronic infections cause by a hepatitis virus, a human immunodeficiency virus (HIV), a human T-lymphotropic virus (HTLV), a herpes virus, an Epstein-Barr virus, or a human papilloma virus.

The Exemplary Embodiments and Example(s) below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXEMPLARY EMBODIMENTS

1. An amphiphilic oligonucleotide conjugate including: a lipophilic component; and directly or indirectly conjugated thereto an immunomodulating oligonucleotide that, if it were not conjugated to the lipophilic component, would suppress TLR7 and/or TLR8 stimulation.

2. The amphiphilic oligonucleotide conjugate of embodiment 1, wherein the lipophilic component includes a phospholipid, a diacyl lipid, a fatty acid, a cholesterol, bile, or a steroid.

3. The amphiphilic oligonucleotide conjugate of embodiment 1 or 2, wherein the lipophilic component includes a linear, branched, or cyclic lipid 8-30 carbons in length.

4. The amphiphilic oligonucleotide conjugate of any one of embodiments 1-3, wherein the lipophilic component includes:

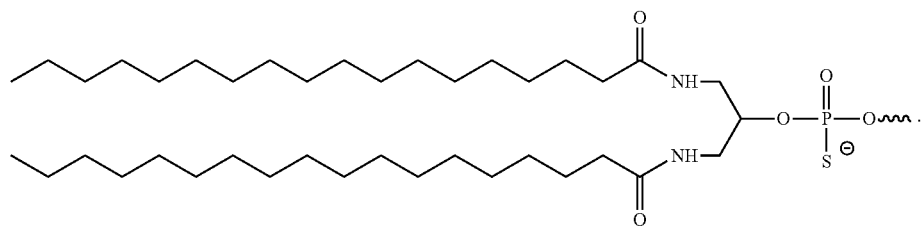

5. The amphiphilic oligonucleotide conjugate of any one of embodiments 1-4, wherein the immunomodulating oligonucleotide includes a oligodeoxynucleotide (ODN).

6. The amphiphilic oligonucleotide conjugate of embodiment 5, wherein the ODN includes 5-50 nucleotides.

7. The amphiphilic oligonucleotide conjugate of embodiment 5, wherein the ODN includes 15-25 nucleotides.

8. The amphiphilic oligonucleotide conjugate of any one of embodiments 1-7, wherein the ODN includes a poly-oligo(dT) of 5-50 nucleotides (T5-T50).

9. The amphiphilic oligonucleotide conjugate of embodiment 8, wherein the ODN includes a poly-oligo(dT) of 18-25 nucleotides (T18-T25).

10. The amphiphilic oligonucleotide conjugate of any one of embodiments 1-9, wherein the ODN includes a phosphorothioate bond or another modified (non-naturally occurring) bond.

11. The amphiphilic oligonucleotide conjugate of any one of embodiments 1-7 or 10, wherein the immunomodulating oligonucleotide includes the sequence of SEQ ID NO: 1, SEQ ID NO: 2, SEQ ID NO: 3, or SEQ ID NO: 4.

12. The amphiphilic oligonucleotide conjugate of any one of embodiments 1-11, further including a linker between the lipophilic component and the immunomodulating oligonucleotide.

13. The amphiphilic oligonucleotide conjugate of any one of embodiments 1-12, wherein the lipophilic component is conjugated to the immunomodulating oligonucleotide at its 5' or 3' terminal end.

14. The amphiphilic oligonucleotide conjugate of any one of embodiments 1-13, including:

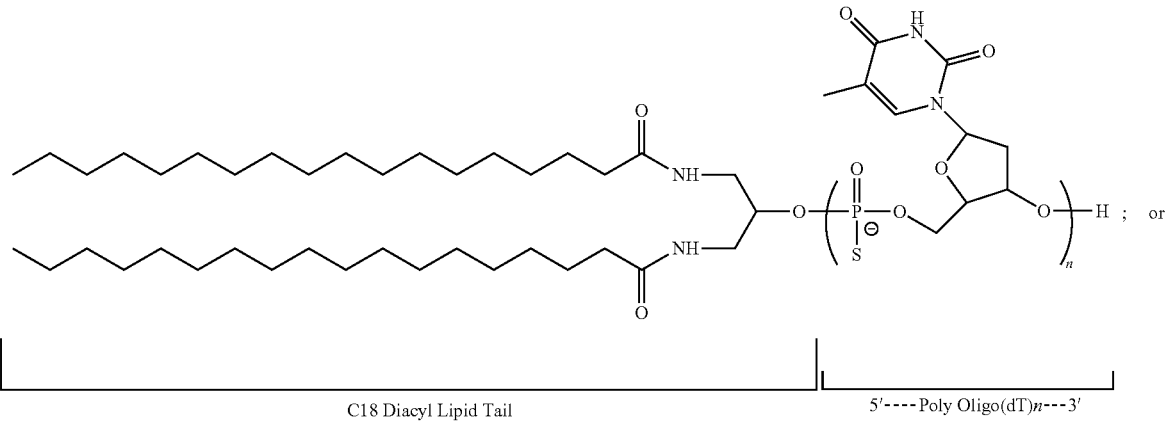

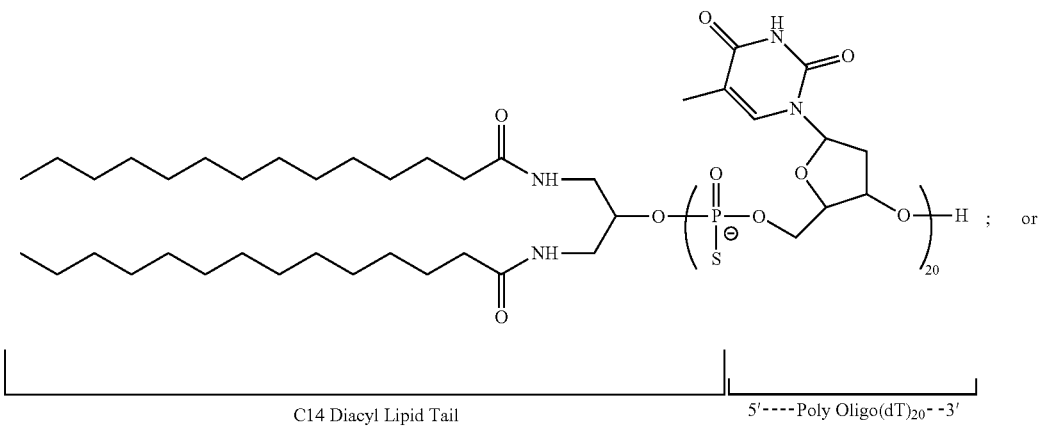

-continued

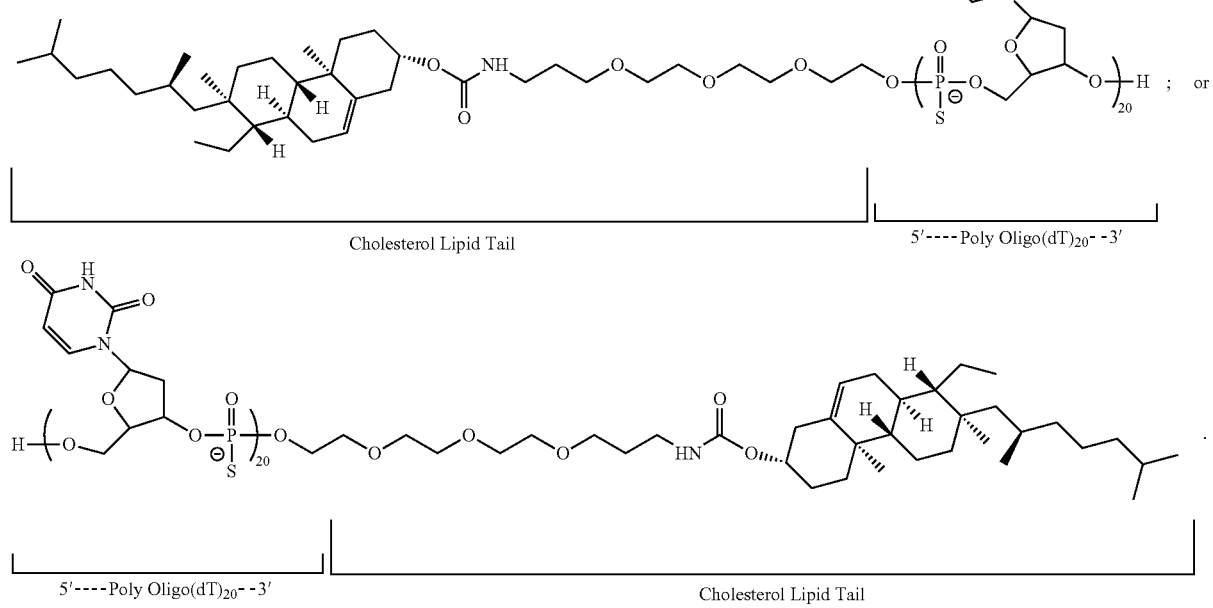

15. Use of the amphiphilic oligonucleotide conjugate of embodiment 1, or any one of embodiments 1-14, to improve efficacy of a vaccine.
16. The use of embodiment 15, wherein improved efficacy includes one or more of increased immunostimulation, increased TLR7 stimulation, increased NF-κB activation in reporter cells, increased cytokine production in primary immune cells, lower $EC_{50}$, reduced toxicity, increased antigen-specific CD8 T cell response, and increased humoral response.
17. The use of embodiment 15 or embodiment 16, which occurs in vivo in the presence of albumin.
18. An immunogenic composition including: an antigen; a TLR7- or TLR8-mediated adjuvant; and an amphiphilic oligonucleotide conjugate of embodiment 1, or any one of embodiments 1-14.
19. The immunogenic composition of embodiment 18, further including at least one element of a delivery system.
20. The immunogenic composition of embodiment 18 or embodiment 19, wherein the antigen includes a viral antigen, a bacterial antigen, a parasite antigen, an allergen, an environmental antigen, or a cancer antigen.
21. The immunogenic composition of any one of embodiments 18-20, wherein the antigen includes a subunit antigen.
22. The immunogenic composition of any one of embodiments 18-21, further including at least one additional adjuvant.
23. The immunogenic composition of any one of embodiments 18-22, wherein the TLR7- or TLR8-mediated adjuvant includes a single-stranded RNA, an oligoribonucleotide (ORN), a base analog, or an imidazoquinolinamine.
24 The immunogenic composition of embodiment 23, wherein the imidazoquinolinamine is imiquimod (R-837; IMQ) or resiquimod (R-848) or gardiquimod (GDQ).
25. The immunogenic composition of embodiment 23, wherein the base analog includes Loxoribine, CL075, CL097, CL264, CL307, or TLR8-506.
26. An enhanced adjuvant composition including: an adjuvant; and the amphiphilic oligonucleotide conjugate of embodiment 1, or any one of embodiments 1-14, in an amount sufficient to enhance an immune response to an antigen when the enhanced adjuvant composition is administered to a mammal.
27. A method of enhancing TLR-mediated activation in a subject in need thereof, including administering to the subject a therapeutically effective amount of the amphiphilic oligonucleotide conjugate of embodiment 1, or any one of embodiments 1-14.
28. A method of improving therapeutic efficacy of an imidazoquinolinamine, including administering the imidazoquinolinamine concurrently with the amphiphilic oligonucleotide conjugate of embodiment 1, or any one of embodiments 1-14.
29. The method of embodiment 28, wherein the imidazoquinolinamine is imiquimod (IMQ) or gardiquimod (GDQ).
30. The method of embodiment 29, wherein improving therapeutic efficacy of IMQ includes inducing a higher level of NF-κB stimulation and/or promoting the secretion of proinflammatory cytokines
31. An amphiphilic oligonucleotide conjugate, composition including an amphiphilic oligonucleotide conjugate, or method of using an amphiphilic oligonucleotide conjugate essentially as described herein.

Example 1: Amphiphilic Oligodeoxynucleotides as Toll-Like Receptor 7 Adjuvant Enhancer The immune system plays a crucial role in protecting the body against microbial pathogens and in restraining the development of cancer. Engineering the immune system to provide protective immunological memory (a procedure called vaccination) has been one of the most successful and cost-effective medical interventions to date, saving millions of lives every year via pediatric and adult immunizations (Berzofsky et al., *Nat Rev Immunol* 1:209-219, 2001). However, most vaccines in use today were developed by techniques that were pioneered more than 100 years ago and do not provide protection in many diseases. For example, although highly effective for combating acute infections such as polio, measles and diphtheria, current vaccination technologies have failed to elicit immune responses that provide protection against chronic infections (e.g. HIV, malaria) and have not succeeded in therapeutic settings (Berzofsky et al., 2001; Pardoll, Nat Rev Immunol 2:229-238, 2002; Irvine et al., Nature Materials 12:978-990, 2013), which are designed to harness the patient's immune system to treat an existing disease (e.g. HIV or cancer).

To generate effective immune responses, vaccination often requires the co-administration of antigens (protein fragments) and adjuvants (substances that boost the vaccine potency). Adjuvants are important in vaccines, where they are necessary to activate antigen presenting cells and facilitate the induction of cytotoxic T lymphocytes (CTLs) and antibodies. Adjuvants boost the vaccine immunity through different mechanisms. For example, adjuvants can function as delivery system, promote uptake and direct antigen presentation, or stimulate pathogens recognition receptors (PRRs). Molecules that can engage the Toll-like receptors (TLRs, one of the PPR families) are particularly powerful adjuvants which initiate innate and adaptive immune responses (Duthie et al., Immuno. Rev. 239:179-196, 2011; Anwar et al., Med Res Rev 39:1053-1090, 2019). However, attempts to develop new generation of adjuvants have been hindered by the fact that many adjuvants, although potent in vitro, lack of the physicochemical and pharmacokinetic properties that are critical in vivo (Anwar et al., 2019; Lynn et al., Nat. Biotech. 33:1201-1210, 2015). For example, the small molecular TLR7/8 agonists immune response modifiers (IRMs) such as imiquimod or gardiquimod, have low molecular weight, are poorly water soluble, induce strong local and systemic inflammatory response and are poorly tolerated in vivo. To date these compounds are restricted to topic use for certain skin diseases and have not been approved as adjuvants for vaccines. As a result, there are a multitude of adjuvants available, but very few of them reach clinical stage.

Systemic lupus erythematosus (SLE) is an autoimmune disease where the host immune system wrongly mounts immune attacks against a large part of healthy tissues. In SLE patients, elevated serum levels of interferon-α (IFN-α) are closely related to disease activity and severity (Barrat et al., J Exp Med 202, 1131-1139, 2005). The increased levels of IFN-α can be induced by DNA and RNA viruses and immune complexes (ICs) that consist of autoantibodies specific to endogenous DNA- and RNA-derived self-antigens (Barrat et al., J Exp Med 202, 1131-1139, 2005). In innate immunity, TLR7 and TLR9 signaling can respectively sense mammalian RNA and DNA in the forms of ICs via pathogen-associated molecular patterns (PAMPs) and thus induce IFN-α production in plasmacytoid dendritic cells (pDC) (Hemmi et al., Nature 408, 740-745, 2000; Heil et al., Science (New York, N.Y.) 303, 1526-1529, 2004). Accordingly, inhibitors specific to TLR7 and TLR9 can be utilized to suppress IFN-α production and thus treat SLE patients. To date, a series of oligonucleotide-based inhibitors of TLR signaling have been developed (Barrat et al., J Exp Med 202, 1131-1139, 2005; Gursel et al., J Immunol (Baltimore, Md.: 1950) 171, 1393-1400, 2003). To leverage the "albumin-hitchhiking" delivery approach, the therapeutic efficacy of lipid-modified ODN A151 was investigated; it showed improved immunosuppressive activity in inhibiting TLR9-mediated immune activation when compared to the unmodified counterpart (Yu et al., Pharmaceutical Research 35, 56, 2018; see also U.S. Patent Publication No. US2019/0015522).

To further expand the pool of lipo suppressive oligodeoxynucleotides (ODNs), the therapeutic benefits of lipid-modified TLR7 inhibitor was investigated. TLR7 is an endosomal receptor which binds viral single-stranded RNA such as RNA of hepatitis B virus, or synthetic guanine-rich RNA base analogs such as R848 and imiquimod (IMQ) (Zhang et al., Immunity 45, 737-748, 2016; Gorden et al., J Immunol 177, 2006). As one of the lead compounds of TLR7 agonists, IMQ has been approved by FDA for topical application, which is effective in treating several major skin tumors and cutaneous metastases (van Seters et al., NEJM 358, 1465-1473, 2008; Ahn & Huang, Am J Clin Dermatol 15, 387-399, 2014). To evaluate the efficacy of lipid-modified immunoregulatory sequence 954 (lipo IRS 954), a dual inhibitor of TLR7 and TLR9 signaling (Barrat et al., J Exp Med 202, 1131-1139, 2005), IMQ was used as a primary ligand to induce TLR7-mediated immune activation.

Surprisingly, it was found that lipo IRS 954 enhanced TLR7-mediated activation instead of showing TLR7-specific immunosuppression. The immune enhancement was also observed in another potent TLR7-specific antagonist, 20-mer thymidine oligodeoxynucleotide (T20) (Gorden et al., J Immunol 177, 2006), showing that lipid-modified T20 (lipo T20) also significantly improved immune activation of IMQ. Interestingly, in the absence of serum albumin, lipo T20 markedly inhibited IMQ-induced activation in Raw-Blue cells, suggesting an indispensable role of albumin in the reversal of biological properties of lipo T20. Moreover, bovine serum albumin (BSA)-T20 conjugate, which was obtained via covalently conjugating T20 to BSA, exhibited potent immunosuppression in TLR7-mediated immune activation. Therefore, lipid modification converted the oligonucleotide-based TLR7 inhibitors into TLR7 adjuvant boosters in the presence of albumin. Because of its small molecular size, unformulated IMQ injected subcutaneously showed little lymph node (LN) accumulation. Instead, IMQ tends to diffuse into the bloodstream and activate the immune system nonspecifically. It was reasoned that lipo T20, with intrinsic LN-targeting capability via "albumin-hitchhiking", might be able to enhance the adjuvant activities of IMQ, allowing dose-sparing and reducing toxicity. As expected, subcutaneous administration of "IMQ/protein antigen" vaccine laced with lipo T20 in mice resulted in a five-fold increase in T-cell priming and enhanced antibody response in comparison to the parent vaccine. Accordingly, lacing vaccine formula with the adjuvant booster is a novel and simple approach to enhance the immunogenicity of molecular vaccines.

It is known that formulation and delivery of TLR agonists can improve their adjuvant efficacy by targeting the immune cells and minimizing the systemic exposure (Shao et al., ACS Nano 9, 16-30, 2015; Li & Guo, Molecules 23, doi:10.3339/molecules23071583, 2018; Irvine et al., Chem. Rev. 115, 11109-11146, 2015). For example, conjugating TLR agonists to protein antigen (Li & Guo, 2018), or co-delivery TLR ligands and antigen with particle-based carriers (Irvine et al., 2015) have been shown to dramatically improve the stimulatory effect of TLR ligands. In these cases, the overall improvements were often attributed to the enhanced spatial and temporal biodistributions. However, unless a rapid release mechanism is implemented, the adjuvant activities per TLR agonist were compromised, or sometimes completely abrogated (Li & Guo, 2018; Liu et al., Nature 507, 519-522, 2014). Here we reported the discovery of an amphiphilic oligonucleotide-based adjuvant enhancer which specifically improves the agonist activities of small molecular TLR7 ligands. Importantly, these amphiphilic oligonucleotides can be administered by simply mixing with FDA approved TLR agonists, eliminating the need for a formulation or delivery system. Thus, use amphiphilic oligonucleotides as adjuvant booster is a novel and simple approach to enhance the immunogenicity of molecular vaccines.

2 Materials and Methods

2.1 Materials

All reagents and commercially available compounds for DNA synthesis were purchased from Glen Research (Sterling, Va.) or Chemgenes (Wilmington, Mass.) and used following the manufacturer's instructions. 3'-Fluorescein amidite (FAM) labeled controlled pore glass was purchased from Allele Biotechnology (San Diego, Calif.). Fatty acid-free BSA was purchased from Sigma-Aldrich. Ovalbumin protein was purchased from Worthington Biochemical Corporation (Lakewood, N.J.). Murine MHC class I tetramer was obtained from MBL International Corporation (Woburn, Mass.). Antibodies were purchased from eBioscience (San Diego, Calif.) or BD Bioscience (San Jose, Calif.). Biotin anti-human CD303 antibody and biotin anti-human CD304 antibody were purchased from Biolegend (San Diego, Calif.). Anti-biotin, microbeads, columns, and magnets were purchased from Miltenyi Biotec (Bergisch Gladbach, Germany). Imiquimod, resiquimod, and Gardiquimod™ were purchased from Cayman Chemical Company (Ann Arbor, Mich.). 1-(4-(Aminomethyl)benzyl)-2-butyl-1Himidazo[4,5-c]quinolin-4amine dihydrochloride was bought from Synnovator, Inc (Durham, N.C.). CL075, TLR8-506, poly I:C and all cell lines were purchased from InvivoGen (San Diego, Calif.). Cy5-labeled T20 was purchased from IDT (Coralville, Iowa). All other reagents were from Sigma-Aldrich and used as received except where otherwise noted.

2.2 Synthesis of Diacyl Lipid Phosphoramidite

The diacyl lipid phosphoramidite was synthesized as previously described (Liu et al., Nature 507, 519-522, 2014). A solution of stearoyl chloride (6.789 g, 22.41 mmol) in 1,2-dichloroethane (50 mL) was added dropwise to a solution of 1,3-diamino-2-dydroxypropane (1.0 g, 11.10 mmol) in the presence of 1,2-dichloroethane (100 mL) and triethylamine (2.896 g, 22.41 mmol). The reaction mixture was stirred for 2 hours at 25° C. and then heated at 70° C. overnight. The reaction mixture was then cooled to 25° C., filtered, and the solid was sequentially washed with $CH_2Cl_2$, $CH_3OH$, 5% $NaHCO_3$ and diethyl ether. The product was dried under vacuum to give the intermediate product as a white solid (yield: 90%). 1H NMR (300 MHz, $CDCl_3$, ppm): δ 6.3 (m, 2H), 3.8 (m, 1H), 3.4-3.2 (m, 4H), 2.2 (t, 4H), 1.6 (m, 4H), 1.3-1.2 (m, 60H), 0.9 (t, 6H). The intermediate product (5.8 g, 9.31 mmol) and N, N-Diisopropylethylamine (DIPEA, 4.2 mL, 18.62 mmol) was then suspended in anhydrous $CH_2Cl_2$ (100 mL). The mixture was cooled on an ice bath and 2-Cyanoethyl N, N-diisopropylchlorophosphoramidite (8.6 mL, 0.47 mmol) was added dropwise under dry nitrogen. After stirring at 25° C. for 1 hour, the solution was heated to 60° C. for 90 min. The solution was washed with 5% $NaHCO_3$ and brine, dried over $Na_2SO_4$ and concentrated under vacuum. The final product was isolated by precipitation from cold acetone to afford 4 g (55% yield) lipid phosphoramidite as a white solid. 1H NMR (300 MHz, $CDCl_3$): δ 6.4 (m, 2H), 3.9 (m, 2H), 3.8 (m, 2H), 3.6 (m, 2H), 3.0-2.9 (m, 2H), 2.6 (t, 2H), 2.2 (m, 4H), 1.6 (m, 6H), 1.3-1.2 (m, 72H), 0.9 (t, 6H). 31P NMR ($CDCl_3$): 154 ppm.

2.3 Synthesis and Purification of Oligonucleotides

All ODN sequences were synthesized using an ABI 394 DNA synthesizer on a 1.0 micromole scale. All lipophilic phosphoramidites were conjugated as a final 'base' on the 5' end of oligos. Lipophilic phosphoramidite was dissolved in dichloromethane and coupled to oligos in DNA synthesizer (15 min coupling time). After the synthesis, DNA was cleaved from the solid support, deprotected, and purified by reverse phase HPLC using a C4 column (BioBasic-4, 200 mm×4.6 mm, Thermo Scientific), 100 mM triethylamine-acetic acid buffer (TEAA, pH 7.5)-methanol (0-5 min, 50-80%; 5-15 min, 80-100%) as an eluent. Lipophilic ODNs typically eluted at 13 min while unconjugated oligos eluted at 7 min. Fluorescein-labeled ODNs were synthesized using 3'-(6-Fluorescein) tagged controlled pore glass. Lipid-conjugated IRS 954 (5'-TGCTCCTGGAGGGGTTGT-3) (SEQ ID NO: 1 shows only the ODN; SEQ ID NO: 6 reflects the lipid modification); Barrat et al., J Exp Med 202, 1131-1139, 2005), T20 (5'-TTTTTTTTTTTTTTTTTTTT-3') (SEQ ID NO: 2) (Gorden et al., J Immunol 177, 8164-8170, 2006; Gorden et al., J Immunol. 177, 6584-6587, 2006; Jurk et al., Euro J Immunol 36, 1815-1826, 2006), ODN 2087 (5'-TCCTGAGCTTGAAGT-3') (SEQ ID NO: 3) (Stunz et al., Euro J Immunol 32, 1212-1222, 2002), and CpG ODN 1826 (5'-TCCATGACGTTCCTGACGTT-3') (SEQ ID NO: 4) (Ballas et al., J Immunol (Baltimore, Md. 1950) 167, 4878-4886, 2001) were synthesized using the above method; these single-stranded DNA sequences were linked via phosphorothioate backbones.

2.4 In Vitro TLR Reporter Cells Stimulation

HEK-Blue™-mTLR7, mTLR8, hTLR7, hTLR8, and RAW-Blue™ cells were purchased from InvivoGen and were used to evaluate bioactivities of lipo ODNs and TLR 7/8 ligands in vitro. All these cell lines were cultured with DMEM supplemented with 10% FBS, 1% P/S and 100 µg/mL Normocin at 37° C. with 5% $CO_2$. In a typical procedure, 2 µM IMQ and 1 µM unmodified T20 or lipo T20 (or lipo IRS 954 or lipo ODN 2087) were added to InvivoGen HEK-Blue™ murine or human TLR7/8 or RAW-Blue™ mouse macrophage reporter cells, both of which are engineered with secreted embryonic alkaline phosphatase (SEAP) reporter gene. After incubating for 24 h, SEAP levels were quantified by developing supernatants with QuantiBlue™ substrate for 1 h and reading absorption at 620 nm, following manufacturer's instructions.

2.5 In Vitro Cellular Uptake and Confocal Imaging

DC 2.4 cells were cultured with RPMI-1640 supplemented with 10% FBS and 1% P/S; Raw-Blue cells were cultured as previously described. 1 µM FAM-labeled unmodified T20 or lipo T20 at 37° C. for 12 h. After incubation, cells were washed twice with 1×PBS by centrifuge at 800×g for 5 min prior to flow cytometry quantification. To visualize in vitro cellular uptake, DC 2.4 cells or Raw-Blue cells were cultured and incubated under the same experimental conditions and were subjected to confocal imaging by Zeiss LSM 510 microscope. To investigate endocytosis pathways, DC 2.4 cells seeded in 12-well plates ($5\times10^5$ cells/well) were pretreated with endocytic inhibitors at 37° C. for 30 min in Opti-MEM and then treated with 1 µM Alexa-647 BSA or 1 µM FAM-labeled T20 and Lipo T20 at 37° C. for 2 h. Inhibitors: 5 µg/mL Filipin; 50 µM EIPA; 300 mM sucrose were tested.

2.6 Albumin-ODN Conjugates

Thiol-terminated T20 or CpG was synthesized by solid-phase coupling of fluorescein-labeled T20 or CpG with C6 S-S CE phosphoramidite (Thiol-Modifier C6 S-S, ChemGenes) at the 5' end of the oligo. 27 mg Bovine serum albumin (BSA, 50 mg/µL in PBS) was co-dissolved with 0.32 mg N-(3-Maleimidopropyloxy) succinimide ester (BMPS, 30 mg/ml in DMSO, Aldrich) and the mixture was agitated at RT for 2 h. Extra BMPS was removed by diluting in PBS solution and passing the mixture through a PD MidiTrap G-25 desalting column (GE Healthcare) and concentrated and further purified by centrifuge filter tube (30K MWCO). 125 nmol of 5'-disulfide-modified fluorescein-T20 or CpG was pre-activated by 1000 nmol TCEP (3,3',3''-Phosphanetriyltripropionic acid, 100 mM in deionized water) and then purified through centrifuge filter tube (30K MWCO). Subsequently, activated T20 or CpG was added to the modified-BSA solution. The mixture was agitated overnight at RT and unconjugated T20 or CpG was removed by configuring filter tube (30K MWCO); free T20 or CpG removal was confirmed by size-exclusion chromatography.

2.7 Preparation of Murine Splenocytes

Spleens were freshly collected from mice and were cut into small pieces. A plunger end of a syringe was used to further disassemble spleen tissues into single cells. The cell suspension was subsequently filtered and washed. Lysing buffer was utilized to remove excessive red blood cells. After two washes, 95% viability of splenocytes was confirmed by trypan blue. Splenocytes were resuspended in RPMI-1640 supplemented with 10% FBS and 1% P/S. Splenocytes were seeded at $1\times10^6$ cells/ml in 200 µL in a 96-well plate. Splenocytes were treated with 2 µM IMQ alone or plus 1 µM T20 or lipo T20 for 24 h under culturing conditions.

2.8 Preparation of Primary Human Cells

Whole blood was obtained from the Red Cross, where healthy volunteers had provided informed consent to donate blood. Peripheral blood mononuclear cells (PBMC) were isolated by density gradient centrifugation using Histopaque-1077 (Sigma-Aldrich). The mononuclear cells were washed twice with cold PBS (1×) and resuspended in completed RPMI-1640 supplemented with 10% FBS and 1% penicillin/streptomycin. PBMC were seeded at $2\times10^6$/ml in 200 µL in a 96-well plate.

Plasmacytoid DC (pDC) monocytes were isolated from PBMC by immunomagnetic bead positive selection using BDCA-4 according to manufacturer's instructions (CD304 (BDCA-4/Neuropilin-1) MicroBead Kit, human; Miltenyi Biotec, Bergisch Gladbach, Germany). Briefly, PBMC were first blocked with human FcR blocking reagent and then incubated with immunomagnetic MACS microbeads, and the labeled cells were collected with Miltenyi columns. The positively selected cells were resuspended in complete RPMI and seeded at $1\times10^6$ cells/ml in 200 µL in a 96-well plate. pDC purity and viability from positively isolated cells and populations of cells were determined by flow cytometry.

2.9 Determination of Secreted Cytokines

Supernatants collected from splenocytes suspension or human PBMC suspension after incubation were separately analyzed for IL-6, IL-12p40, TNF-α, and IFN-α by ELISA following manufacturer's instructions.

2.10 In Vivo Immunization

C57BL/6 mice (6-8 weeks) were immunized by a homologous prime-boost regimen: animals were primed on day 0 and boosted on day 14 with 50 µg Ovalbumin and 15 µg IMQ mixed with or without 6.2 nmol lipo T20 dissolved in PBS. The volume of all vaccine injections was 100 µL/animal. All injections were performed subcutaneously at the base of the tail.

2.11 Tetramer Staining

Seven days after the final immunization, blood samples were collected. Red blood cells were lysed by Ammonium-Chloride-Potassium (ACK) lysing buffer. Cells were then blocked with Fc-blocker (anti-mouse CD16/CD32 monoclonal antibody) and stained with SIINFEKL peptide (SEQ ID NO: 5) loaded phycoerythrin-labeled tetramers (Beckman Coulter) and anti-CD8-APC (ebioscience) for 30 min at 4° C. Cells were washed twice, resuspended in FACS buffer, and analyzed on Attune Focus flow cytometer. Analysis typically gated on live CD8+, Tetramer positive cells.

2.12. Intracellular Cytokine Staining

Peripheral blood was lysed with ACK buffer and washed with PBS twice. Purified cells were seeded in 96-well round-bottomed plates and pulsed with 10 µg/mL OVA peptide SIINFEKL (SEQ ID NO: 5) for 2 h at 37° C. in T-cell media (RPMI-1640, 10% FBS, 50 µM β-mercaptoethanol, 1% P/S), followed by the addition of brefeldin A for 4 hours. Cells were stained with anti-CD8-APC and then fixed using Cytofix following the manufacturer's instructions. Next, cells were washed and permeabilized. Intracellular staining for anti-IFN-γ-PE and anti-TNF-α-FITC was performed following the manufacturer's instructions and cells were analyzed by Attune Focus flow cytometer.

2.13 ELISA for OVA-Specific IgG

Mice were bled, and blood samples were collected. Serum anti-OVA IgG levels were determined by ELISA: 96-well plates were coated overnight with 10 µg/ml OVA in PBS and blocked with 1% BSA in PBS. After incubation of serum samples for 1 h at a series of dilutions, plates were washed with PBS/1% Tween-20. Goat anti-mouse IgG conjugated to Horseradish peroxidase (HRP) was added at 1 µg/ml for 30 min. Plates were washed with PBS/1% Tween-20 and ELISA was developed by (3,3',5,5'-Tetramethylbenzidine) (TMB, ebioscience). The reaction was stopped by 1M $H_2SO_4$ and the absorbance was read at 450 nm and 570 nm using a plate reader.

2.14 Statistical Analysis

All plots show mean values and error bars represent the SEM. One-way analysis of variance (ANOVA), followed by a Bonferroni post-test, was used to compare >2 groups. *, $p<0.05$; , $p<0.01$; *, $p<0.001$; ns, not significant unless otherwise indicated. Statistical analysis was performed using GraphPad Prism software (San Diego, Calif.).

3 Results and Discussion

Figure 1B:
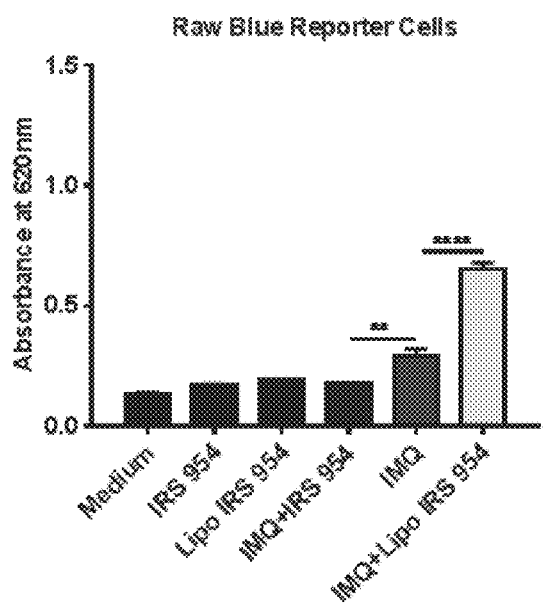

3.1 Lipid Conjugation Specifically Reverses Oligonucleotide-Based TLR7 Inhibitors Previous findings demonstrated that lipid-modified oligonucleotide-based TLR9 inhibitor was more potent and efficacious than unmodified oligo in targeting LNs and suppressing CpG-induced immune activation (Yu et al., *Pharmaceutical Research* 35, 56, 2018). Following subcutaneous injection, lipid-modified oligonucleotides efficiently accumulated in the draining lymph nodes by binding and trafficking with endogenous albumin protein (Liu et al., *Nature* 507, 519-522, 2014; Yu et al., *Pharmaceutical Res.* 35: 56, 2018). Inspired by that prior work, the current study was aimed to take advantage of lipid functionalization in other oligonucleotide-based TLR inhibitors to further expand the pool of lipo suppressive ODNs. The therapeutic efficacy of lipid-modified IRS 954 in suppressing TLR7-mediated immune activation and alleviating the severity of SLE was investigated. Imiquimod (IMQ; FIG. 1A) was first used to stimulate TLR7-mediated immune activation in Raw-Blue reporter cells. For the initial experiments, Raw Blue cells-a murine RAW 264.7 macrophage cell line which expresses secreted embryonic alkaline phosphatase (SEAP) under the control of an NF-κB and AP-1, were used. Raw Blue cells express many toll-like receptors, including TLR-7, TLR-8, and TLR-9. The immunosuppressive capability of unmodified or lipo IRS 954 was determined by quantifying the level of TLR7-induced NF-κB activation. Incubating Raw Blue cells with imiquimod (IMQ, a TLR-7 ligand) resulted in secretion of NF-κB (FIG. 1B). However, in the presence of IRS 954, no detectable NF-κB was observed, suggesting IRS 954 blocked the IMQ stimulation (FIG. 1B). Unexpectedly, while lipid modified IRS 954 (lipo IRS 954) alone has no activity in Raw Blue cells, combining lipo IRS 954 with IMQ led to more than twofold increase in TLR-7-mediated activation (FIG. 1B). These results clearly demonstrated that lipid modification transformed IRS 954, an immune inhibitory ODN which blocks IMQ-mediated TLR-7 stimulation, into an adjuvant enhancer, which augments the activation of TLR-7 by IMQ. The results surprisingly showed that lipo IRS 954 markedly enhanced TLR7-mediated activation, while the unmodified IRS 954 itself remained immunosuppressive toward TLR7 signaling (FIG. 1B).

Figure 1C:
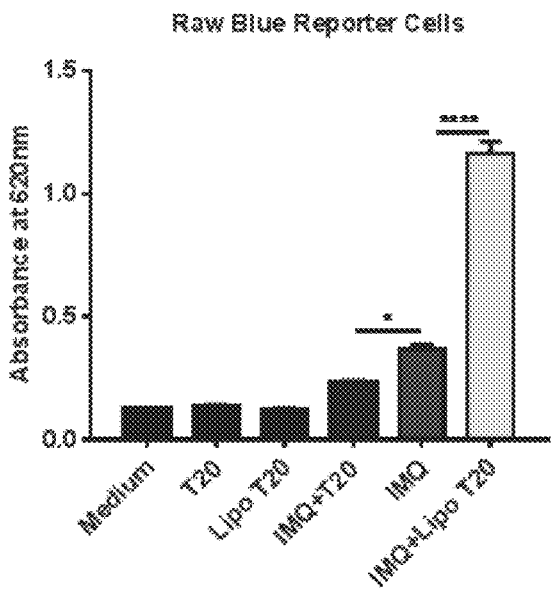
Figure 1D:
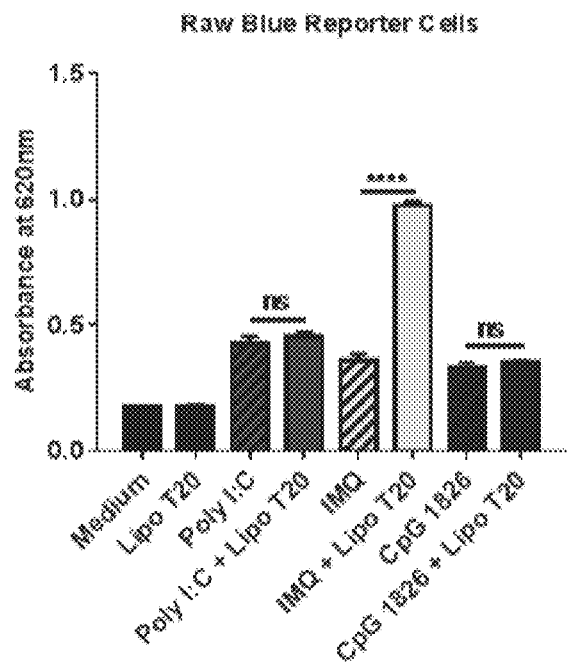

Based on these compelling results, it was hypothesized that lipid modification might be used to reverse the immunological properties of oligonucleotide-based TLR7 inhibitors. To test this hypothesis, the diacyl (C18) lipid tail was conjugated to another classic oligonucleotide-based TLR7 inhibitor, 20-mer polythymidine oligodeoxynucleotide (T20; a classical TLR-7 inhibitor which suppresses both murine and human TLR-7 activation)), to generate lipo T20. This compound was then tested following previous experimental settings. Compared to lipo IRS 954, lipo T20 was even more potent, enhancing the immunostimulatory activities of IMQ 5-fold. In contrast, unmodified T20 was suppressive toward IMQ stimulation, lowering the NF-κB activation by 2 folds (FIG. 1C). A minimum concentration of 1 µM of lipo T20 was found to be required for optimal enhancement (data not shown). The enhancement of NF-κB activation by lipo T20 appeared to be TLR7 ligand specific, as no enhancement was observed when Raw-Blue cells were stimulated by CpG ODN (a TLR9 ligand) and Poly I:C (a TLR3 ligand) (FIG. 1D). Collectively, it was found that lipid conjugation could specifically reverse the inhibitory effect of oligonucleotide-based TLR7 inhibitors.

3.2 the Role of Albumin in the Mechanism of Action

Figure 2D:
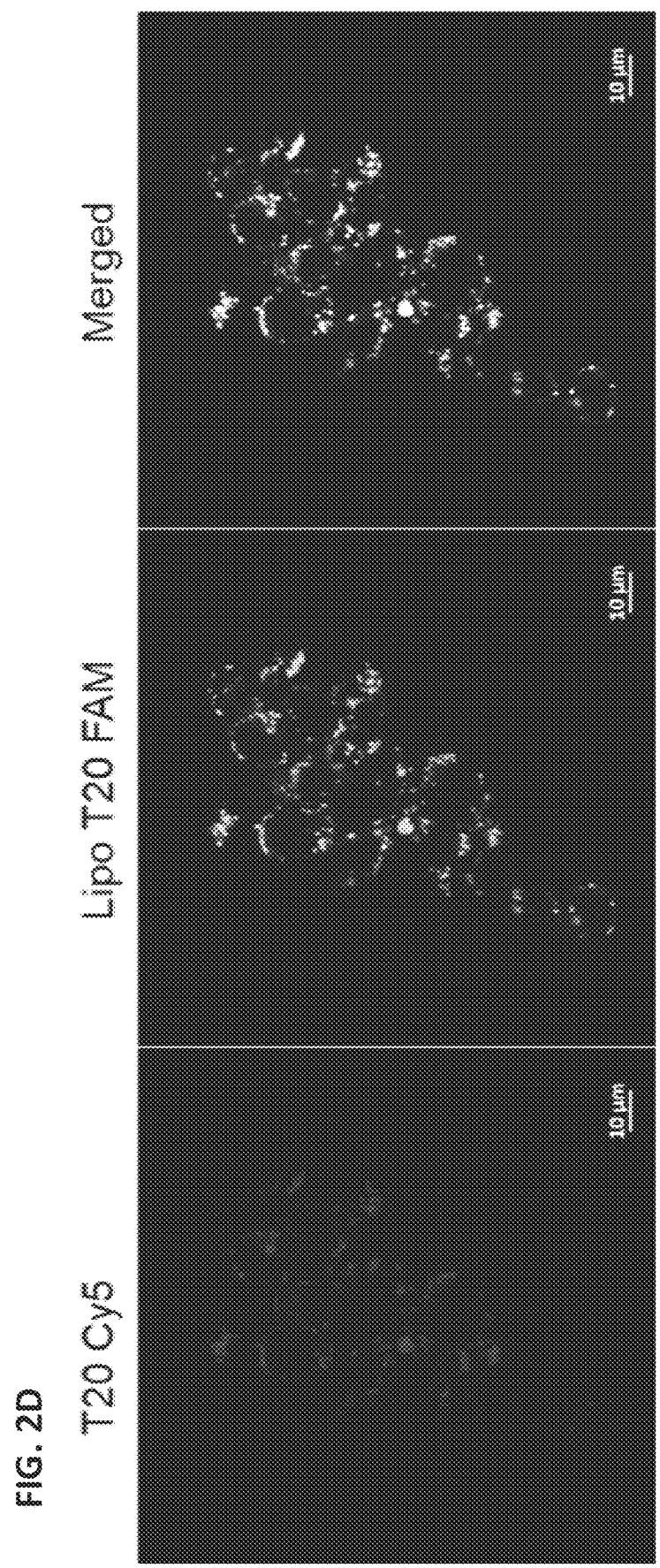

Structurally, lipo T20 might be stimulatory due to the lipid moiety. To test whether the lipid tail can stimulate cells, the same diacyl lipid was conjugated to oligo-mimicking "hexaethyleneglycol" blocks via DNA synthesizer. The amphiphilic polymer lipo (EG)$_{48}$ has a length comparable to lipo T20. Lipid tail itself did not affect IMQ-induced activation (FIG. 2A). Thus, replacing oligo with a non-nucleotide ethylene glycol repeats showed no augmentation of IMQ stimulation in Raw Blue cells, suggesting a nucleotide sequence is required. According to previous studies, lipid conjugation typically resulted in increased cellular uptake. The results here also showed that DC 2.4 cells preferentially internalized more lipo T20 than unmodified T20 over 24 h incubation (FIG. 2B). Based on this, it was speculated that quantitatively increased cellular uptake of T20 might contribute to the qualitative reversal of lipo T20's immunosuppressive properties. However, high-dose T20, five times more concentrated than lipo T20, exhibited significantly enhanced inhibition in IMQ-elicited activation (FIG. 2C), suggesting that enhanced uptake was not responsible for the improved stimulation. In addition, lipid modification did not alter cellular localization of T20, as demonstrated in confocal imaging of DC 2.4 cells treated with 1 µM Cy5-labeled T20 and FAM-labeled lipo T20 simultaneously (FIG. 2D).

Figure 3A:
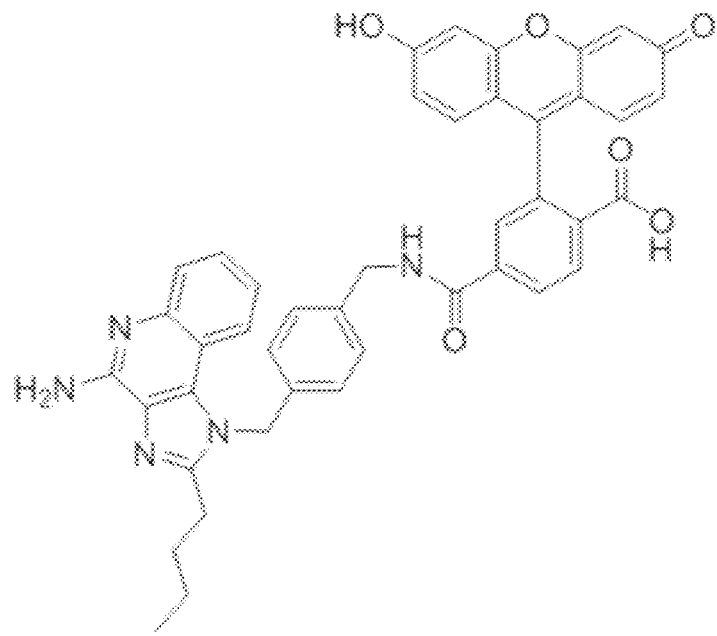
FIGS. 3A-3B (FIG. 3A) Structure of FITC labeled-IMDQ and flow cytometry analysis of Raw-Blue reporter cells treated with 2 μM FITC-IMDQ alone or in combination with 1 μM T20 or lipo T20, (FIG. 3B) Representative confocal images of DC 2.4 cells which were treated with 2 μM Cy5-labeled IMDQ alone or in combination with 1 μM T20 or lipo T20 for 24 h and then washed and stained with 50 nM LysoTracker Green and 300 nM DAPI (4', 6-diamidino-2-phenylindole) following manufacturer's instructions. Scale bar: 10 μm. Data show the mean values ±SEM. *, $p<0.05$; , $p<0.01$; *, $p<0.001$; ****, $p<0.0001$; ns, not significant by one-way ANOVA with Bonferroni post-test.
Figure 3A:
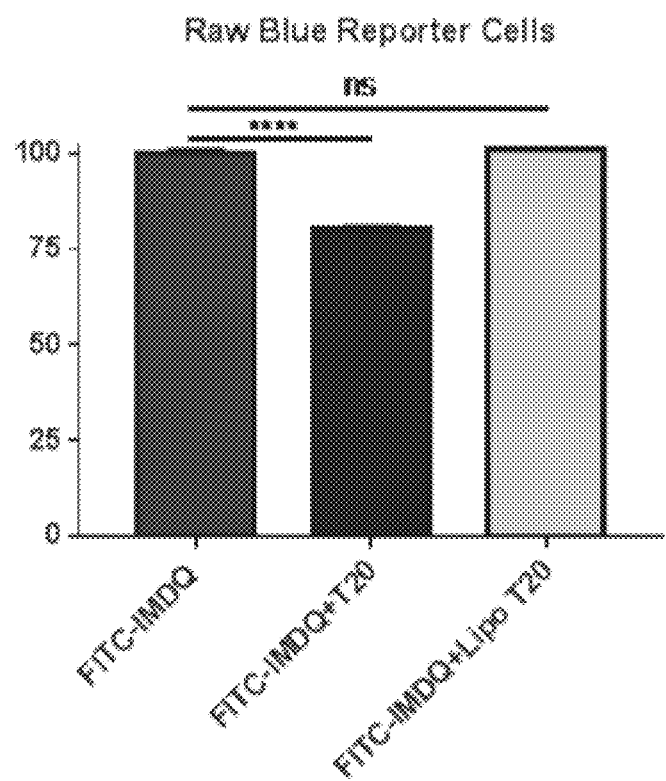
Figure 3B:
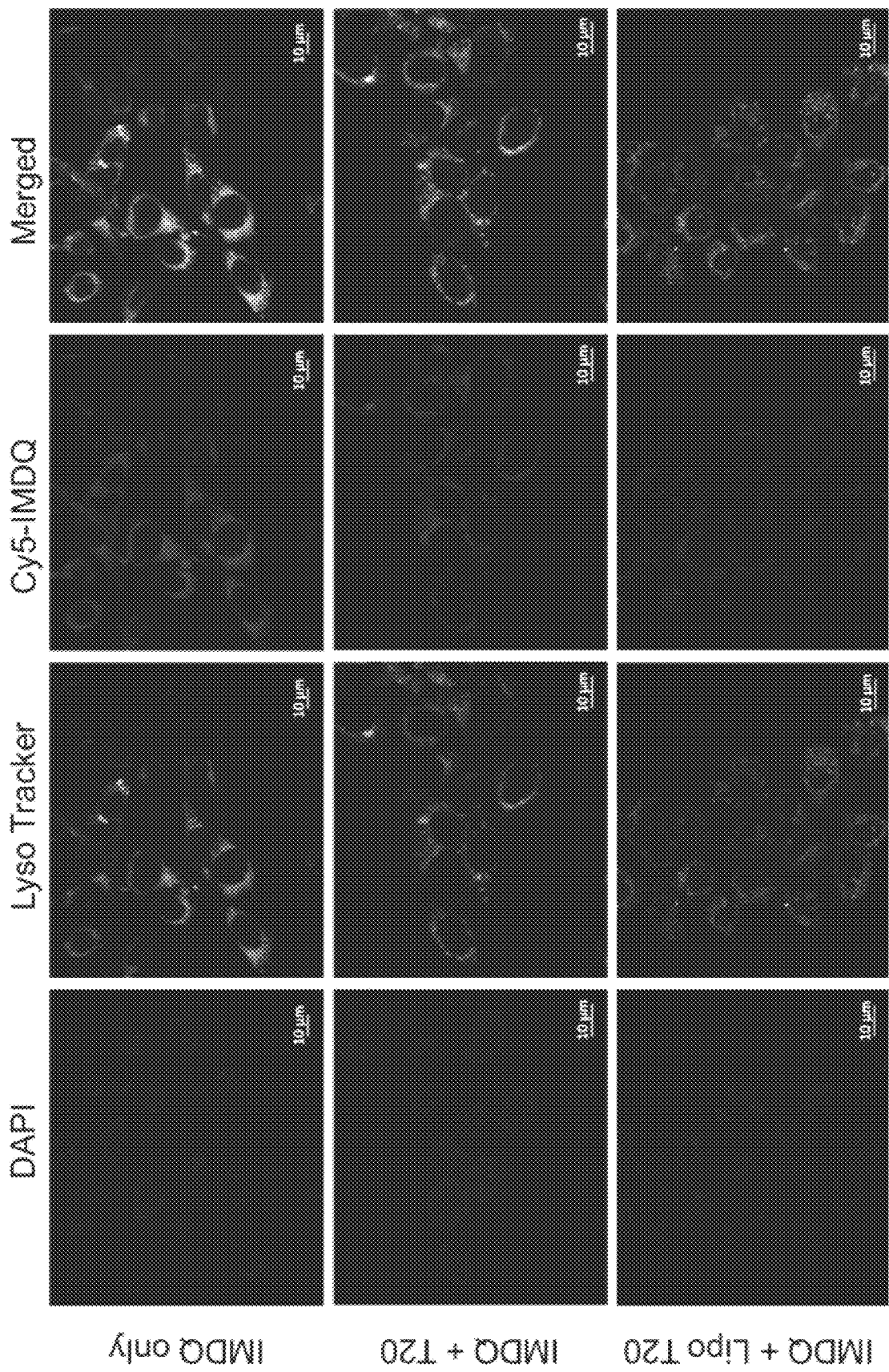

It was previously reported that poly-thymidine could interact with TLR7 ligands like IMQ (Gorden et al., *J Immunol* 177, 8164-8170, 2006). Therefore, it was postulated that lipo T20, with uptake-facilitating lipid tail, might promote cellular uptake of TLR7 ligands via ODN-drug intercalation and subsequently enhanced IMQ-induced activation. To verify this possibility, a functionalizable TLR7 analog of IMQ, 1-(4-(Aminomethyl) benzyl)-2-butyl-1Himidazo[4,5-c]quinolin-4amine (IMDQ), was used for quantification of cellular uptake and fluorescence imaging. Flow cytometry data indicated that neither T20 nor lipo T20 increased cellular uptake of FITC-labeled IMDQ (FIG. 3A). Besides, confocal imaging indicated that IMDQ was primarily in the endosomal-lysosomal compartment in the presence of T20 or lipo T20 (FIG. 3B). Taken together, the data shown here demonstrated that lipid conjugated T20 is a TLR7 adjuvant enhancer which dramatically improves the immunostimulatory effect of IMQ.

Figure 4A:
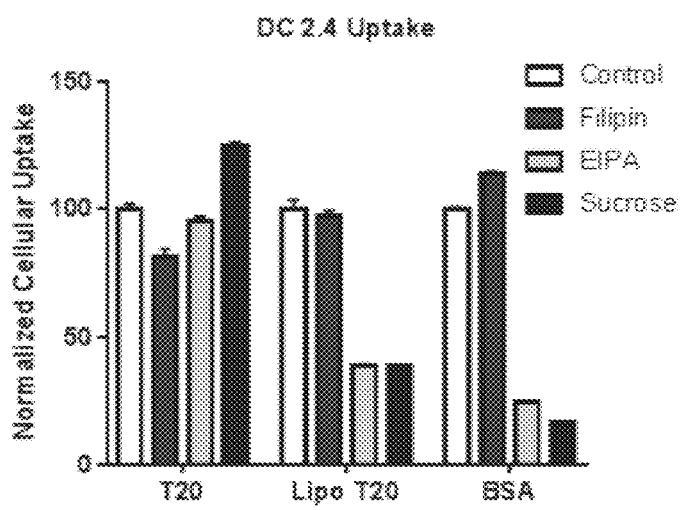
FIGS. 4A-4D.

As lipo T20 contained a lipophilic domain which enabled avid "albumin-binding", it was reasonable to ask whether albumin was playing a role in enhancing IMQ stimulation by lipo T20. In fact, the culture medium was normally supplemented with fetal bovine serum (FBS) containing excessive albumin relative to the quantity of lipo T20 utilized, so it was highly possible that lipo T20 would bind to serum albumin (FBS) once added to culture medium. As part of the proof to support this hypothesis, it was observed that the endocytosis pathway of lipo T20 exactly mimicked that of BSA, which was internalized mainly via macropinocytosis (EIPA) and clathrin-mediated endocytosis (Sugar) in DC 2.4 cells (FIG. 4A). This observation agreed with previous studies on endocytosis of lipid-modified ODN conjugates and albumin (Ugarte-Uribe et al., *Bioorganic & medicinal chemistry* 25, 175-186, 2017; Commisso et al., *Nature* 497, 633-637, 2013; Yumoto et al., *Am J Physiol*. Lung cellular and molecular physiology 290, L946-955, 2006).

Figure 4B:
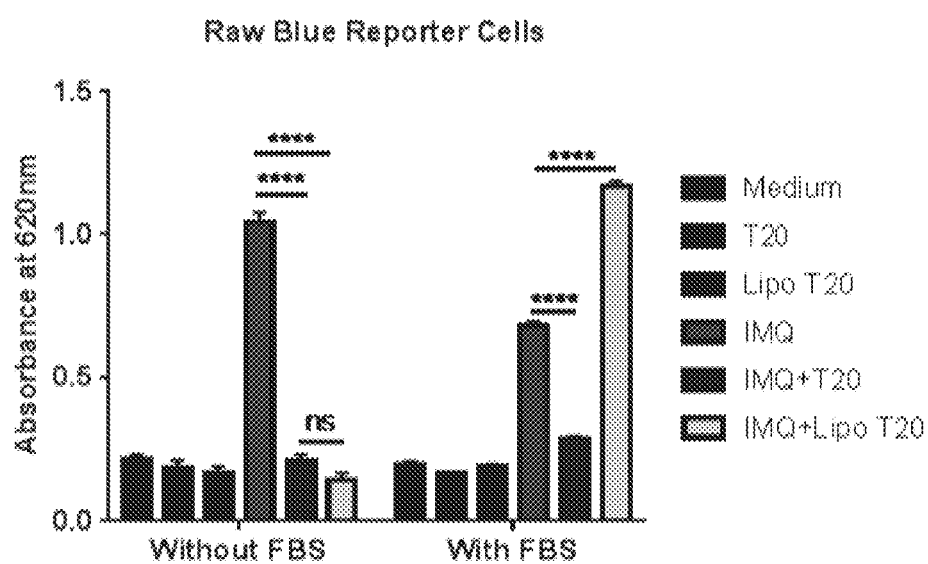
Figure 4C:
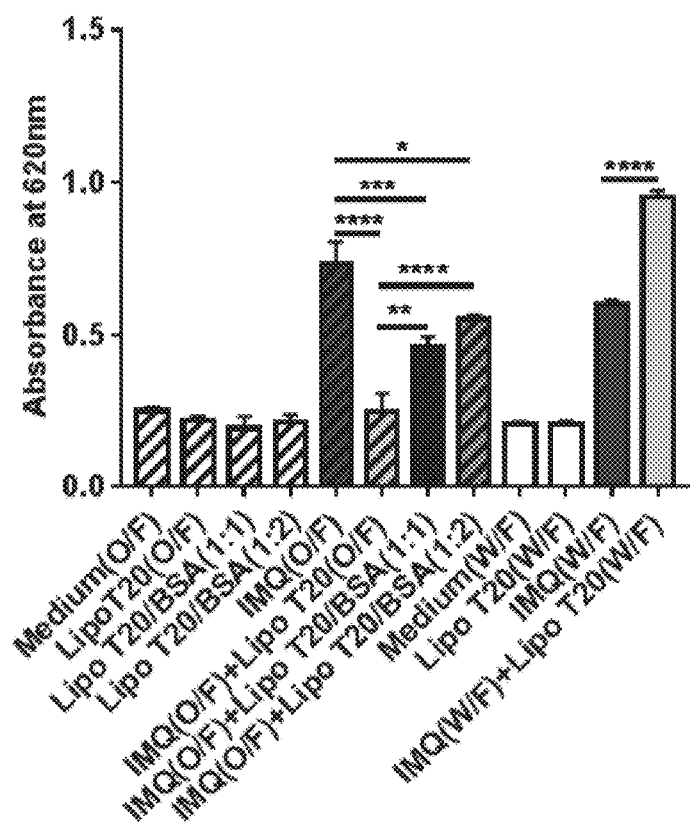

To further determine the role of albumin in the enhanced stimulation of IMQ, Raw-Blue cells were seeded overnight and then stimulated as previously described using the serum-free medium. Interestingly, lipo T20 completely suppressed IMQ-induced NF-κB activation under FBS-free culture conditions, indicating that albumin played an important role in the effect of lipo T20 on TLR 7 stimulation (FIG. 4B). Meanwhile, cell viability was ruled out as a potential factor for downregulated NF-κB stimulation by confirming that the survival rate of Raw-Blue cells was unchanged under the FBS-free culture condition (FIG. 4C).

Figure 4D:
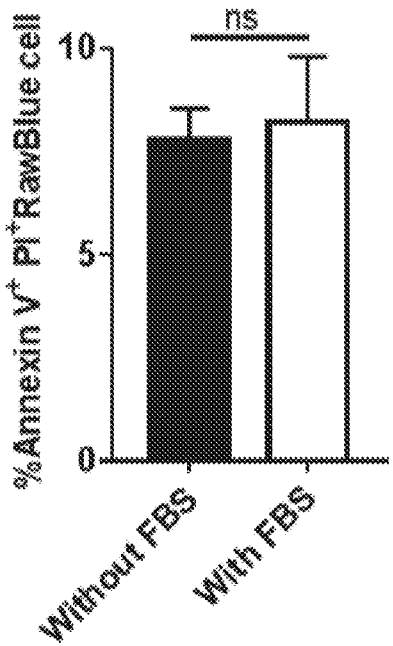
Figure 4D:
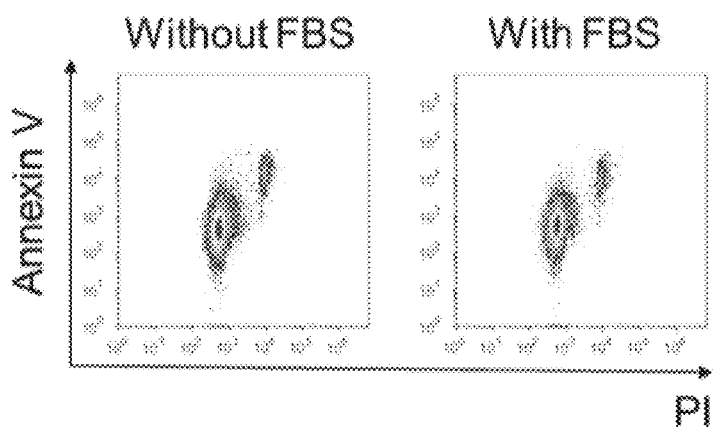

Since lipo ODN is able to hijack albumin and subsequently accumulates in APCs residing in LNs (Liu et al., *Nature* 507, 519-522, 2014), forming stable albumin-lipo ODN complexes in physiological condition is a prerequisite for survival on their thorny way to LNs and lymphoid APCs. Similarly, lipo T20 should be able to complex with albumin under FBS-supplemented culture condition before being transported into cells. Besides, research into erythrocytes insertion revealed that amphiphilic polymer was unable to massively insert into the plasma membrane in the presence of blood serum. Collectively, these reasonings pointed to a "fact" that lipo T20 was transferred into cells in the form of lipo T20-albumin complex. To verify this postulation, lipo T20 was pre-incubated with BSA at a ratio of 1:1 and 1:2 for 1 h and then pre-seeded Raw-Blue cells were treated with 1 µM BSA-complexed lipo T20 under FBS-free condition. The results clearly showed that lipo T20's capability of suppressing IMQ-induced activation was progressively abrogated as the ratio of pre-complexed BSA increased (FIG. 4D). This confirmed that the reversal of lipo T20's biological capability of inhibiting TLR7 signaling primarily resulted from albumin which formed albumin-lipo T20 complex via noncovalent interaction.

Figure 5C:
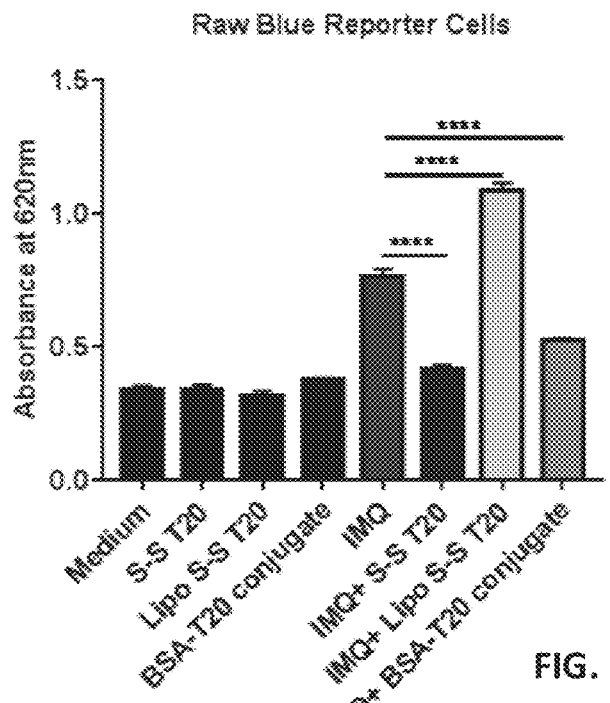
Figure 5D:
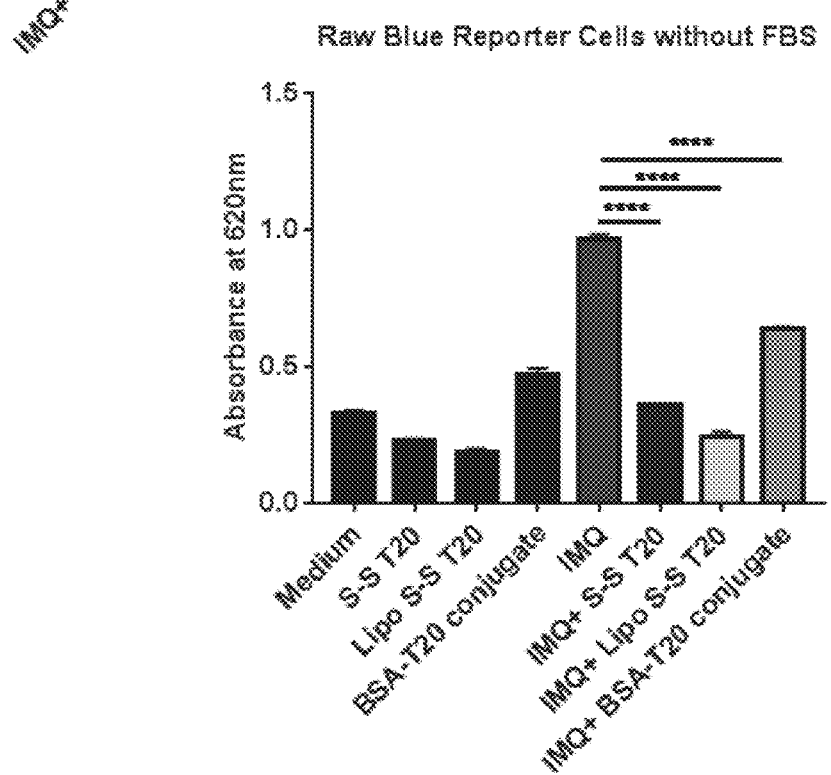

Additionally, both T20 and lipo T20 were shown to be colocalized with lysosomes regardless of the presence of FBS, suggesting that albumin did not significantly affect lipo T20's intracellular destination (FIGS. 5A, 5B). However, a covalently-synthesized BSA-T20 conjugate failed to reverse the intrinsic properties of T20 under both FBS-supplemented and FBS-free culture conditions, as it greatly suppressed IMQ-induced activation (FIGS. 5C, 5D). Accordingly, the reversal of lipo T20's immunological property was more than due to the endocytosis pathway via hijacking albumin and was not due to quantitatively increased cellular uptake.

3.3 Optimization of TLR7 Adjuvant Booster

To optimize TLR7 stimulation enhancing efficacy, a series of lipo poly-oligo-deoxythymidine (poly-Oligo(dT)) molecules were synthesized to treat Raw-Blue cells along with IMQ (FIG. 6A). As shown in FIG. 6B, lipo T20 or lipo T25 mixed with IMQ induced the highest level of NF-κB stimulation. In contrast, lipo T10 showed little effect on IMQ-mediated activation, while lipo T50 slightly suppressed TLR7 signaling. ODNs conjugated with short diacyl lipids, such as C12 and C14 lipid chains, were less effective in targeting LNs due to relatively weak hydrophobic interaction between lipid tails and albumin (Liu et al., Nature 507, 519-522, 2014). However, C14 lipid-modified T20 was observed to give a comparable level of immune activation when mixed with IMQ in vitro (FIG. 6D). In addition, it was found that lipo T20 was unable to enhance IMQ-induced activation once the ratio of lipo T20 to IMQ was less 1:10, while no further potency-enhancing effect was observed when this ratio was greater than 5:10 (FIG. 6D).

Figure 6E:
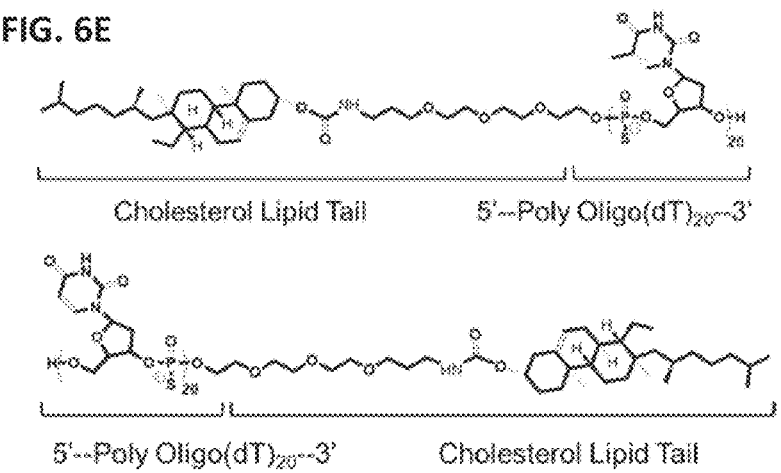
Figure 6F:
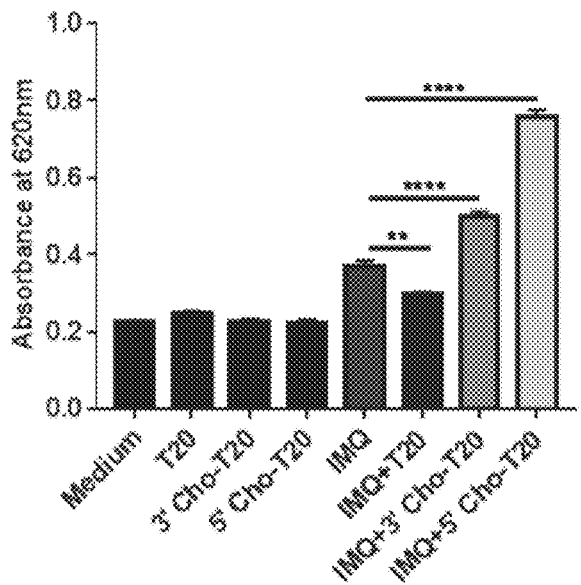
Figure 6G:
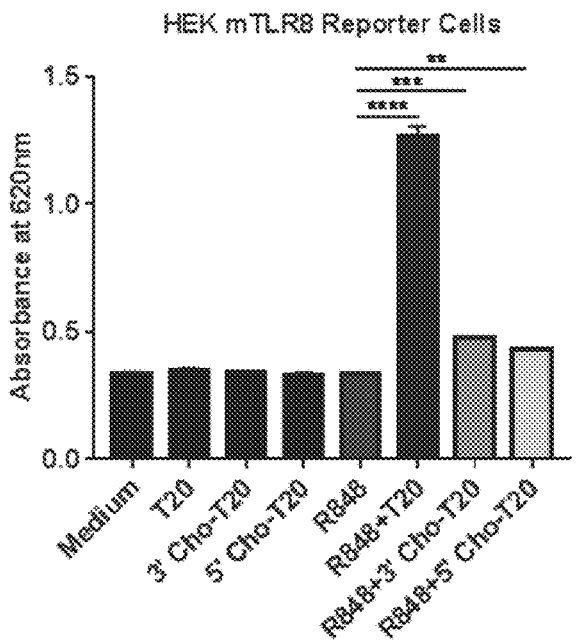

Although most lipo ODNs were modified at 5' terminal of the ODN due to simplicity and cost of synthesis, 3'-terminal modification might give different levels of effects, as reported on the modification of CpG oligonucleotides. To test whether lipid modification at 3' terminal of T20 would affect immune modulation, 5'- and 3'-conjugated lipo T20 was synthesized by using a 5'-cholesterol phosphoramidite and a 3'-cholesterol beads respectively (FIG. 6E). Since T20 itself was a TLR8 booster as well as a TLR7 inhibitor, murine TLR7 and TLR8 reporter cells were used separately for NF-κB stimulation assay. The results revealed that both 5'- and 3'-modified T20s were able to significantly enhance IMQ-induced stimulation in murine TLR7 cells, while both were functionally compromised after modification and unable to activate resiquimod (R848)-elicited murine TLR8 signaling (FIGS. 6F, 6G). Together, these data demonstrated that lipid poly-oligo(dT) with 20-25-mer was the optimal structure to induce the highest level of TLR7-mediated NF-κB activation, and T20 modified with less hydrophobic lipid tail, compared to C18 lipid chain, at either 5' or 3' terminal was able to reverse the TLR7-specific suppression.

3.4 Immune Modulation on TLR7 and TLR8 Reporter Cells

It is known that certain oligonucleotides especially thymidine rich ODNs modulate the stimulation of action TLR-7 and 8 by small molecular ligands (Gorden et al., J Immunol. 177:8164-8170, 2006; Gorden et al., J. Immunol. 177:6584-6587, 2006; Jurk et al., Euro. J Immunol. 36:1815-1826, 2006). T20, for example, has been shown to significantly increase the activation of TLR-8, but completely abolish the activation of TLR-7 when co-incubated with small molecular IRMs (Gorden et al., J Immunol. 177:8164-8170, 2006; Gorden et al., J. Immunol. 177:6584-6587, 2006; Jurk et al., Euro. J Immunol. 36:1815-1826, 2006). To investigate the modulatory effect of lipo T20 on small molecule TLR agonists, murine TLR-7 or TLR-8 transfected HEK293 cells were treated with small molecular TLR ligands. Three categories of TLR ligands are selected: imiquimod (IMQ) which selectively activates TLR-7, CL075 which selectively activates TLR-8, and R848 which is a dual ligand activating both TLR-7 and TLR-8. Raw Blue cells which respond to both murine TLR-7 and TLR-8 are also included to assess the overall modulatory effect. half-maximal effective concentration ($EC_{50}$) and potency of several classic TLR7/8 ligands were evaluated in murine TLR7 and TLR8 reporter cells.

Figure 7A:
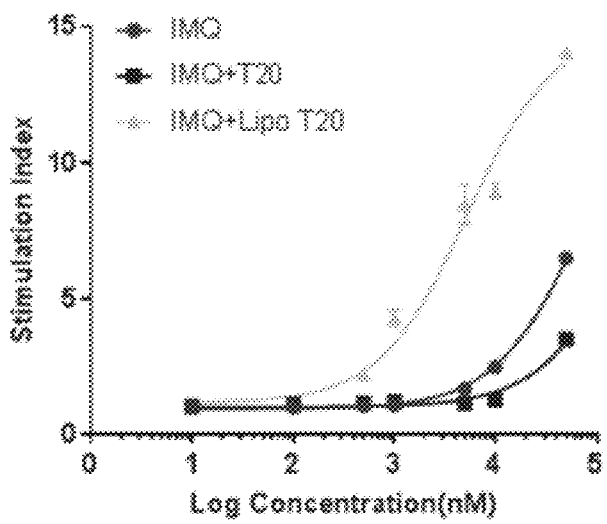
FIGS. 7A-7I (FIGS. 7A-7C) HEK mouse TLR7 (mTLR7) reporter cells were stimulated with IMQ, CL075, R848 at indicated concentrations alone or in combination with 1 µM T20 or lipo T20 for 24 h, NF-κB activation was quantified by measuring the SEAP levels in the supernatant.
Figure 7B:
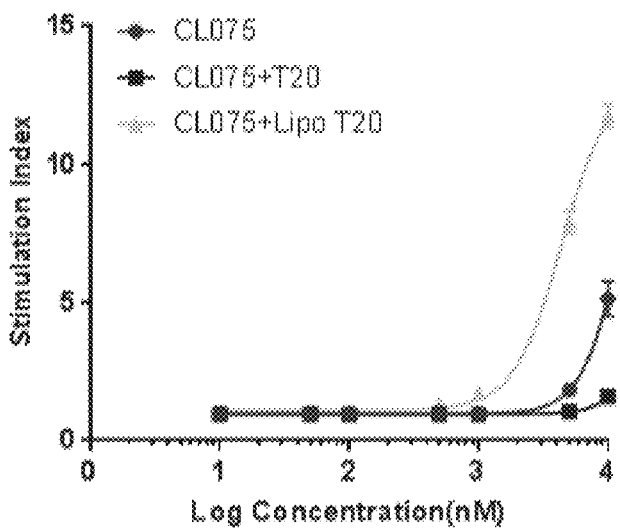
Figure 7C:
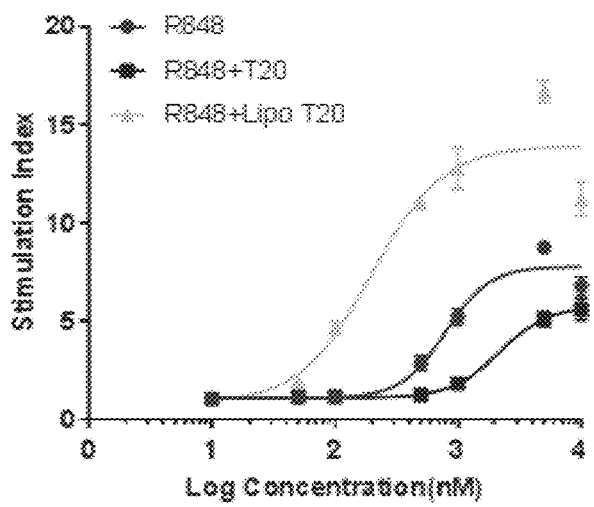
Figure 7D:
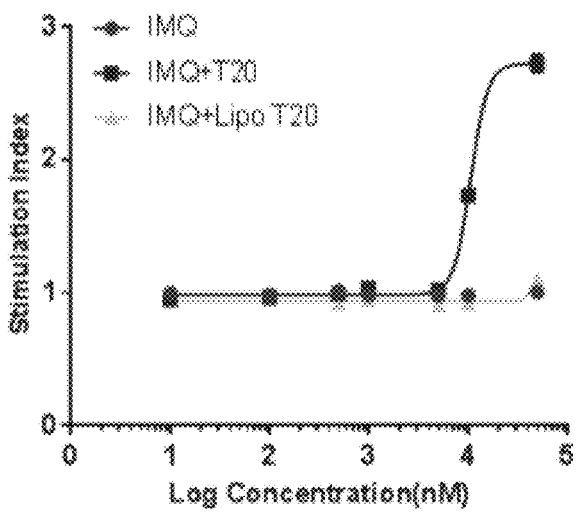
Figure 7E:
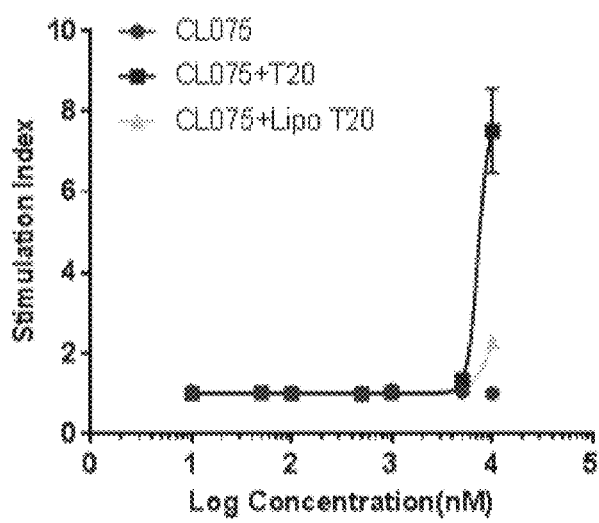
Figure 7F:
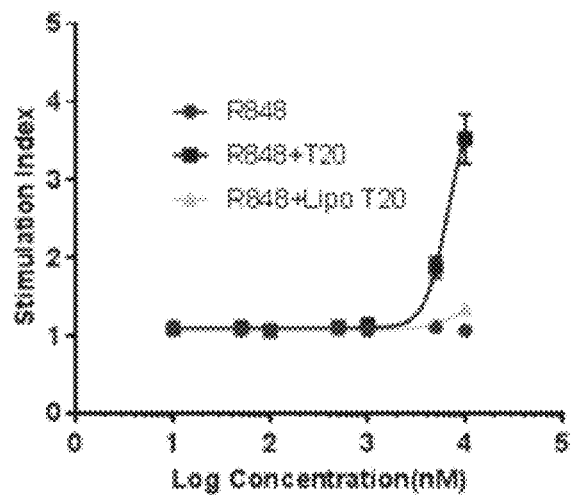
Figure 7G:
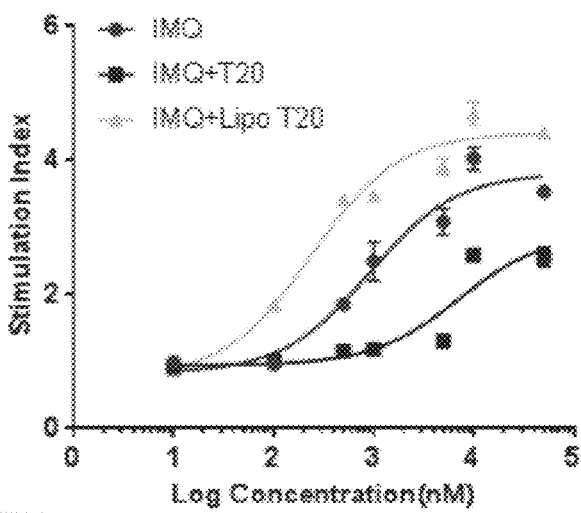
Figure 7H:
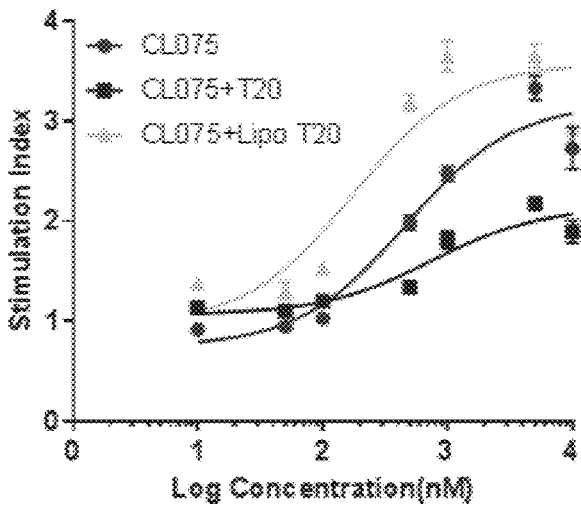
Figure 7I:
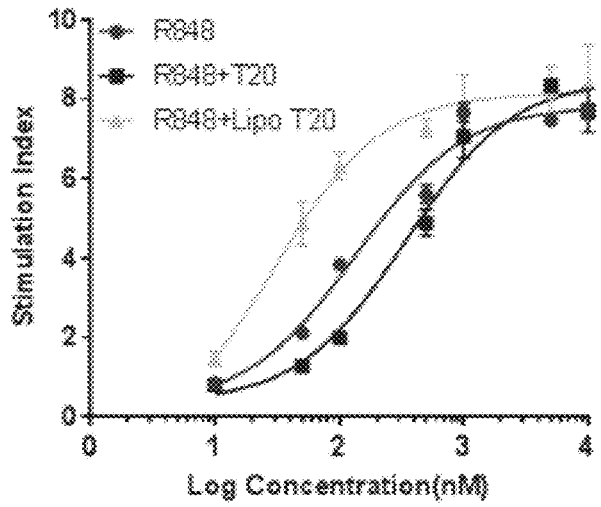

Dramatically different modulatory effects of T20 and lipo T20 upon TLR-7/8 stimulation by different small molecular T20 upon TLR-7/8 stimulation by different small molecular ligands were observed. Soluble IMQ, CL075, and R848 activated mTLR-7 at different concentrations (FIGS. 7A-7C). Consistent with previous reports (Gorden et al., J Immunol. 177:8164-8170, 2006; Gorden et al., J. Immunol. 177:6584-6587, 2006; Jurk et al., Euro. J Immunol. 36:1815-1826, 2006), addition of 1 µM of T20 suppressed the TLR-7 activation in murine TLR-7 transfected HEK cells (FIGS. 7A-7C). In contrast, 1 µM of lipo T20 dramatically enhanced the potency of TLR-7 activation, reducing the $EC_{50}$ by several logs FIGS. 7A-7C). The levels of stimulation of murine TLR-8 by small molecule ligands were low, even at high ligand concentrations (FIGS. 7D-7F). However, the addition of T20 increased the potency of TLR-8 stimulation by these compounds, though the augmented effect was only seen at relatively high ligand concentrations. Lipo T20, however, had largely no effect on the TLR-8 stimulation, only showing a slightly increase at high ligand concentrations (FIGS. 7D-7F). Finally, the overall stimulation of these IRMs in the presence of lipo T20 or T20 were evaluated in Raw Blue cells (FIGS. 7G-7I). All the IRMs showed a concentration dependent activation of Raw Blue cells. However, T20 exhibited a suppressive effect on all the TLR ligands tested. In contrast, in all settings, lipo T20 enhanced the overall NF-κB stimulation. These data clearly demonstrated lipo T20, but not T20, could act as an adjuvant enhancer to improve the immune stimulation of TLR-7 (FIGS. 7G-7I).

Figure 8A:
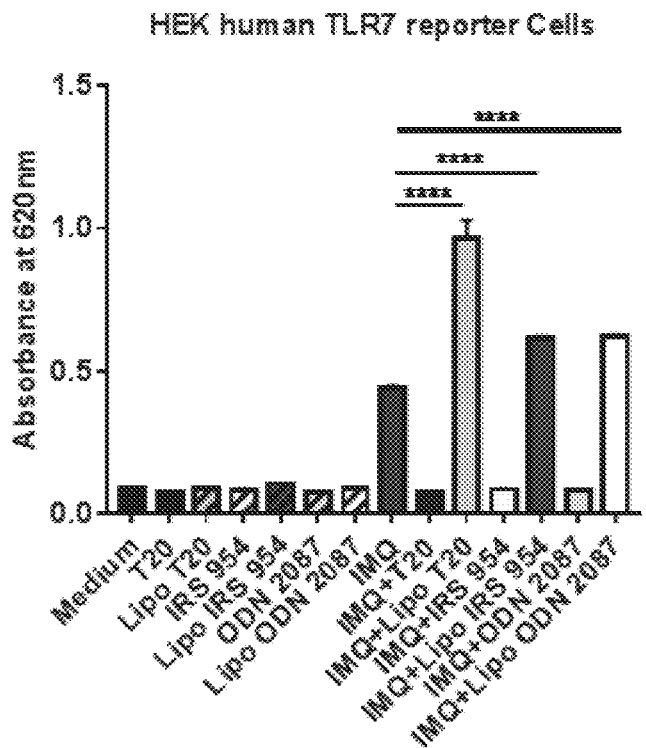
FIGS. 8A-8D.
Figure 8B:
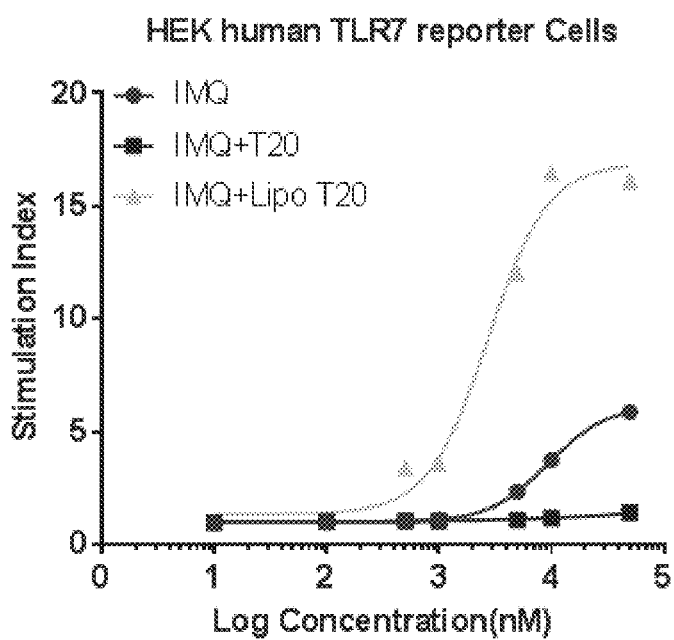
Figure 8C:
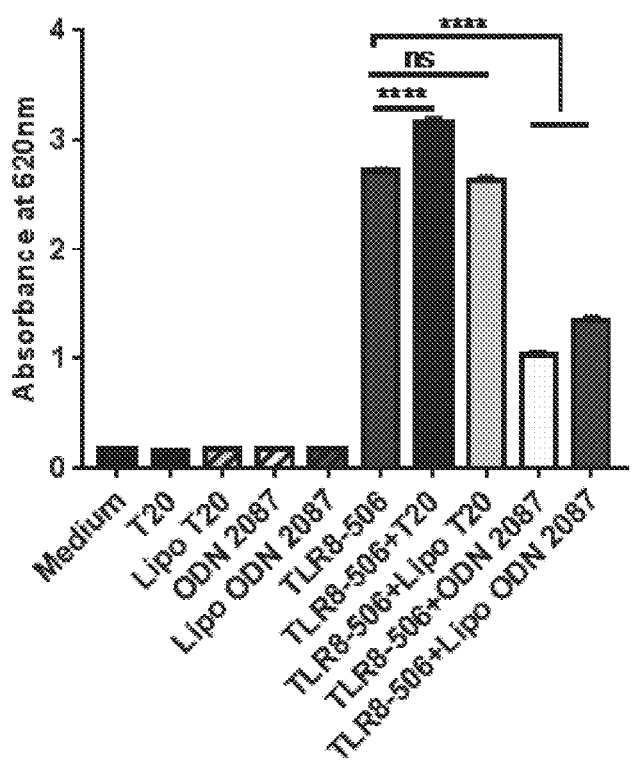
Figure 8D:
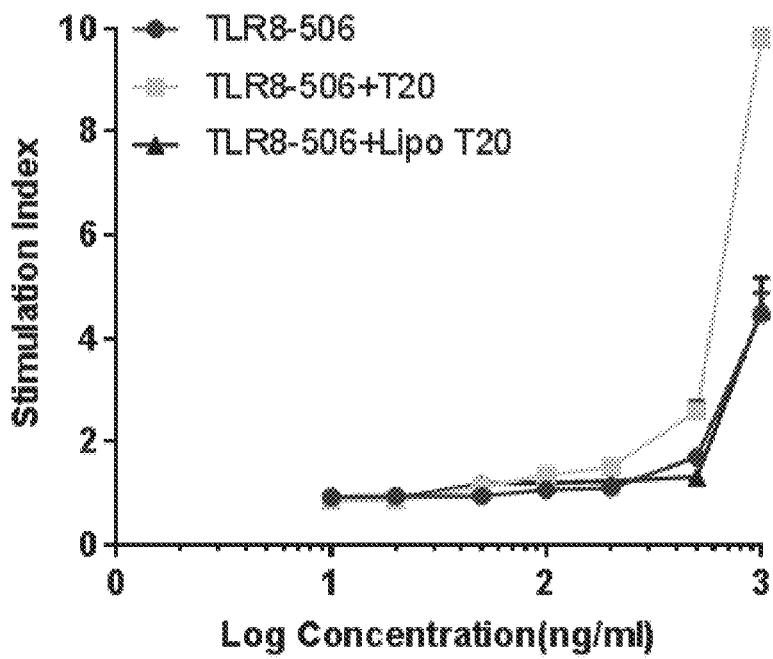

The above results highlight the augmenting effect of lipo T20 on murine TLR-7 stimulation. Whether lipo T20 could improve the activation of human TLR-7 in combination with small molecular TLR-7 agonists was investigated next, as human and murine TLR-7/8 share many similarities in genetic sequence and function. HEK293 cells transfected with human TLR7 or 8 were used. The cells were stimulated with IMQ in the presence of several inhibitory oligonucleotides reported in the literature. Besides lipo T20 and lipo IRS 954, lipid modified ODN 2087, originally developed as a human TLR-7 and -8 inhibitor, also markedly enhanced IMQ-mediated NF-κB stimulation (FIG. 8A), but the strongest augmentation was induced by lipo T20. In contrast, all the unmodified ODNs maintained their inhibitory function, reducing the NF-κB secretion to basal levels (FIG. 8A). We then plotted the IMQ dose response curve in human TLR-7 transfected HEK293 cells. As shown in FIG. 8B, addition of 1 µM lipo T20 dramatically improved the potency and overall magnitude of NF-κB stimulation. Similar to previous observation in murine TLR-7 expressing cells (Gorden et al., J Immunol. 177:8164-8170, 2006; Gorden et al., J. Immunol. 177:6584-6587, 2006; Jurk et al., Euro. J Immunol. 36:1815-1826, 2006), low concentration of unmodified T20 ODN completely abrogated the immune activation by IMQ (FIG. 8B). The addition of T20 enhanced the stimulation of TLR8-506 in human TLR-8 transfected HEK cells (FIG. 8C). In contrast, lipo T20 exhibited no effect on the TLR-8 signaling, showing similar activation to TLR8-506 alone (FIGS. 8C, 8D). In addition, both lipo IRS 954 and lipo ODN 2087 partially inhibited the TLR-8 signaling (FIG.

8C). In summary, depending on the specific sequences, lipid conjugated ODNs dramatically enhance TLR-7 activation and either have no effect (for lipo T20) or partially inhibit (for lipo IRS 954 and lipo ODN 2087) TLR-8 activation when administered with small molecule TLR agonists.

3.5 Ex Vivo Evaluation of Adjuvant Booster

Figure 9A:
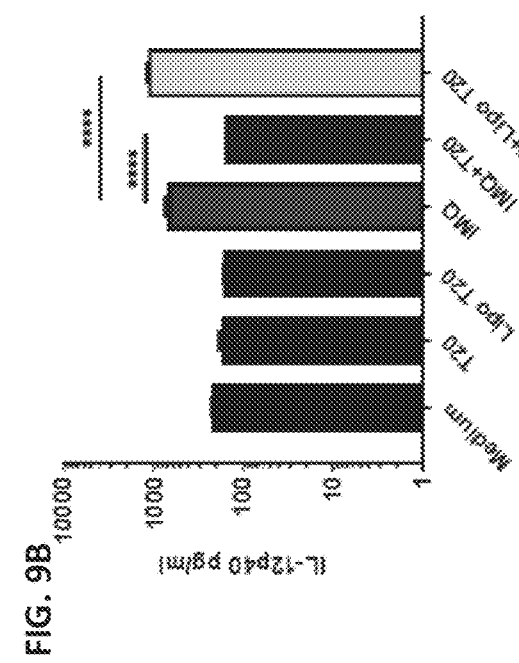
FIGS. 9A-9I (FIGS. 9A-9D) Murine splenocytes were stimulated with 2 µM IMQ alone or in combination with 1 µM T20 or lipo T20 for 24 h, and the inflammatory cytokines and type I IFN secreted by splenocytes including IL-6 (FIG. 9A), IL-12p40 (FIG. 9B), TNF-α (FIG. 9C), IFN-α (FIG. 9D) were measured by ELISA.
Figure 9B:
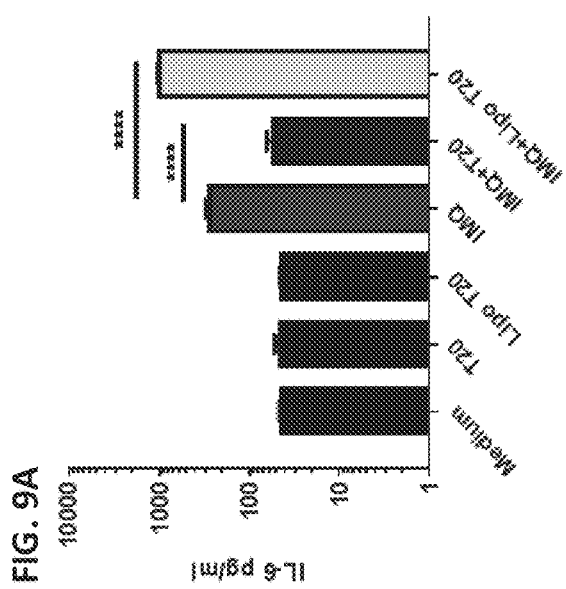
Figure 9C:
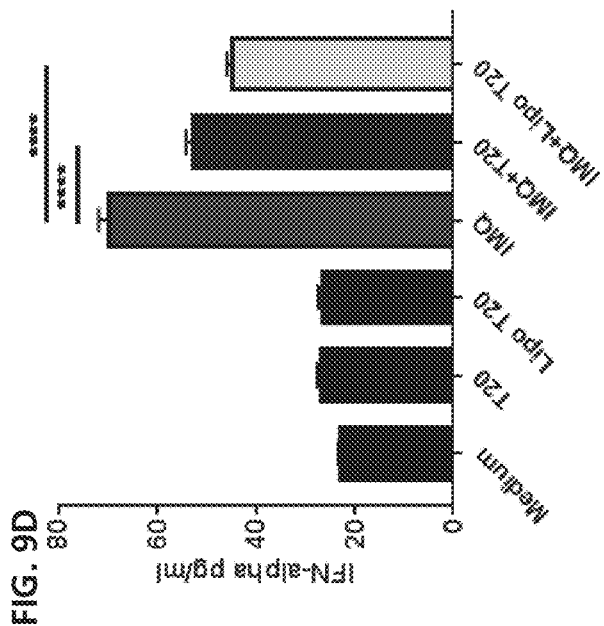
Figure 9D:
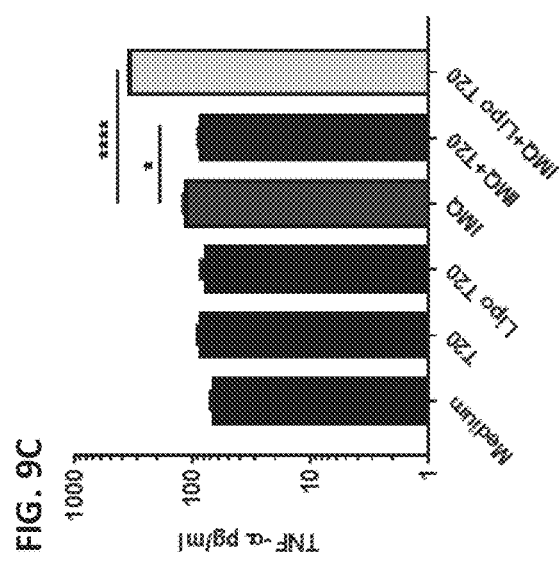

To evaluate the adjuvant enhancing activities of lipo T20 in primary immune cells, we isolated splenocytes from mice spleens and stimulated them with IMQ as previously described in TLR7/8 reporter cells. Consistent with our previous findings in the reporter cells, lipo T20 markedly potentiated the potency of IMQ by upregulating the production of NF-κB-signaled pro-inflammatory cytokines including IL-6, IL-12p40, and TNF-α, while IMQ mixed with T20 led to a significantly lower level of pro-inflammatory cytokines compared with IMQ alone (FIGS. 9A-9C). Interestingly, we observed that both T20 and lipo T20 decreased the production of IFN-α induced by IMQ (FIG. 9D). As secretion of IFN-α from pDC was mainly regulated through IRF7 signaling but independent of NF-κB activation (Blasius & Beutler, *Immunity* 32, 305-315, 2010), the results suggested that lipo T20 primarily intensified TLR7-signaled NF-κB activation but was still able to inhibit TLR7-mediated production of IFN-α.

Figure 9E:
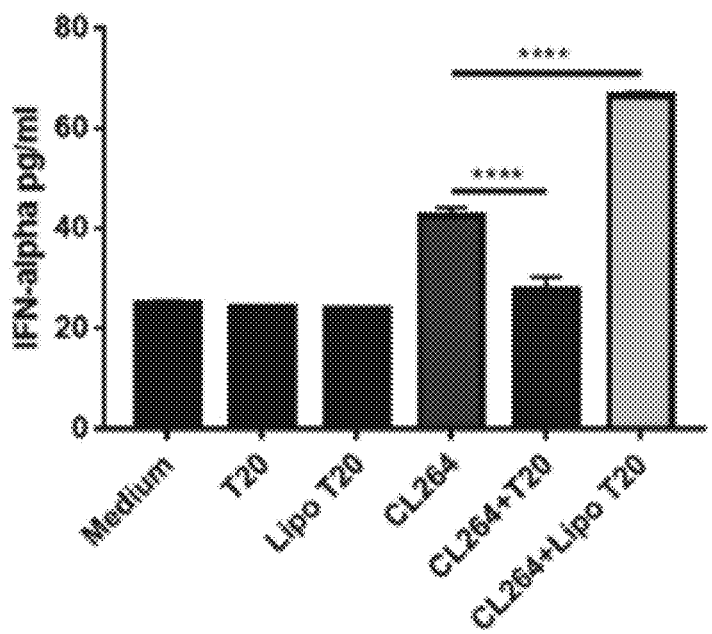
Figure 9F:
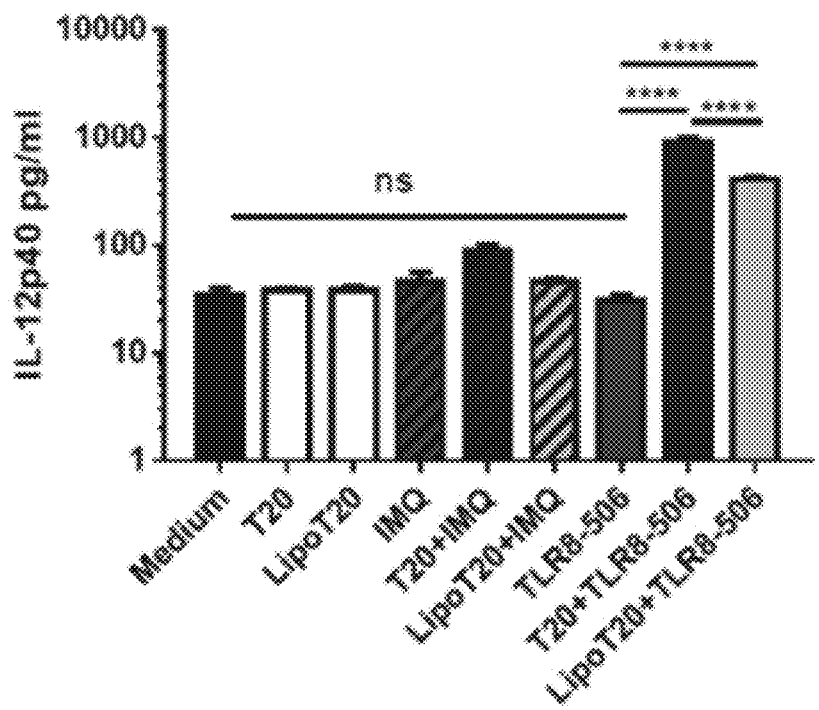

Addition of low concentration of T20 completely abrogated IFN-α production. However, in the presence of lipo T20, a significant increase of IFNα was observed. When PBMC were incubated with TLR8-506, a human TLR-8 specific ligand, both T20 and lipo T20 were able to augment the IL-12 production (FIGS. 9E, 9F). Although the detail mechanism(s) of action remain to be investigated, these results suggest that lipo T20 can enhance the stimulatory effect of small molecule TLR agonists in both murine and human primary cells.

Figure 9G:
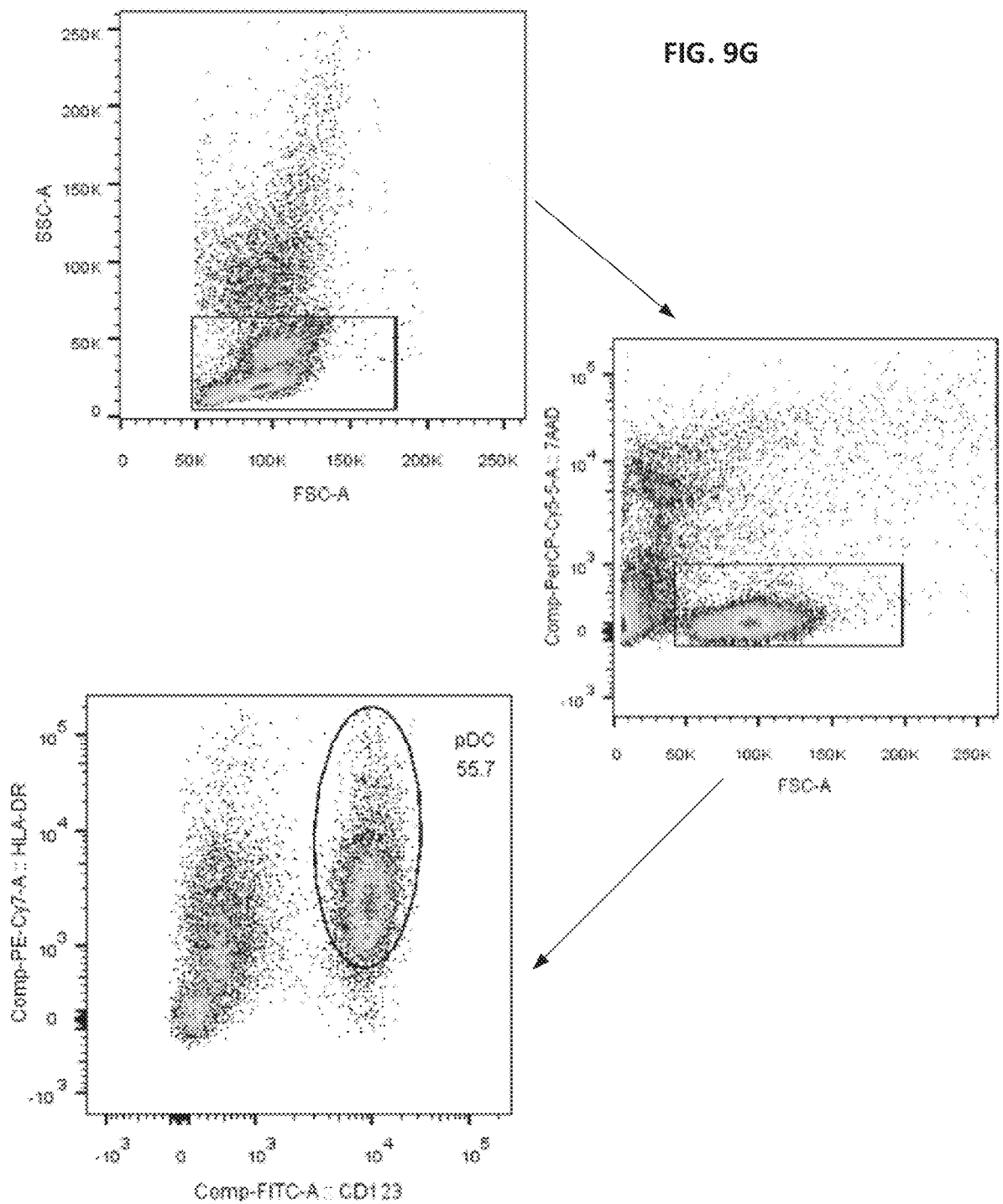
Figure 9I:
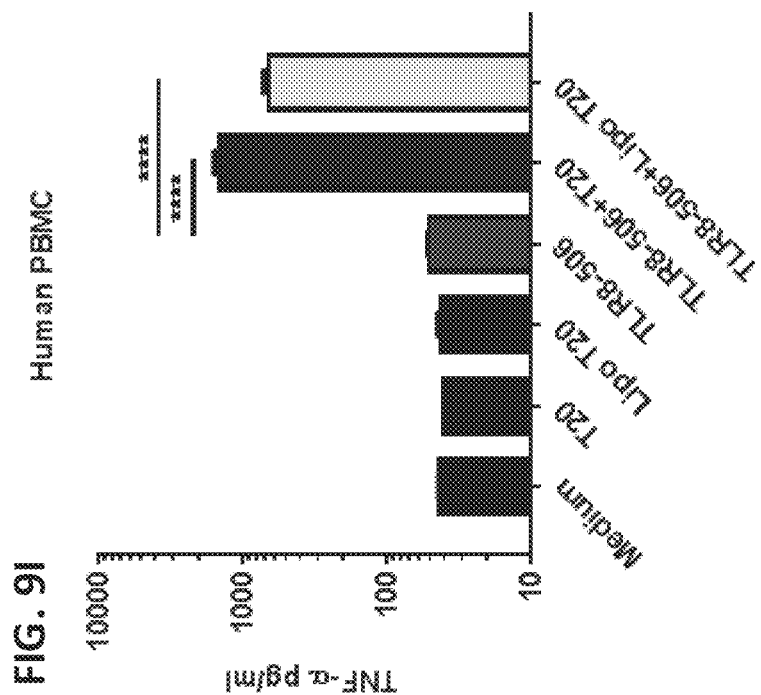
Figure 9H:
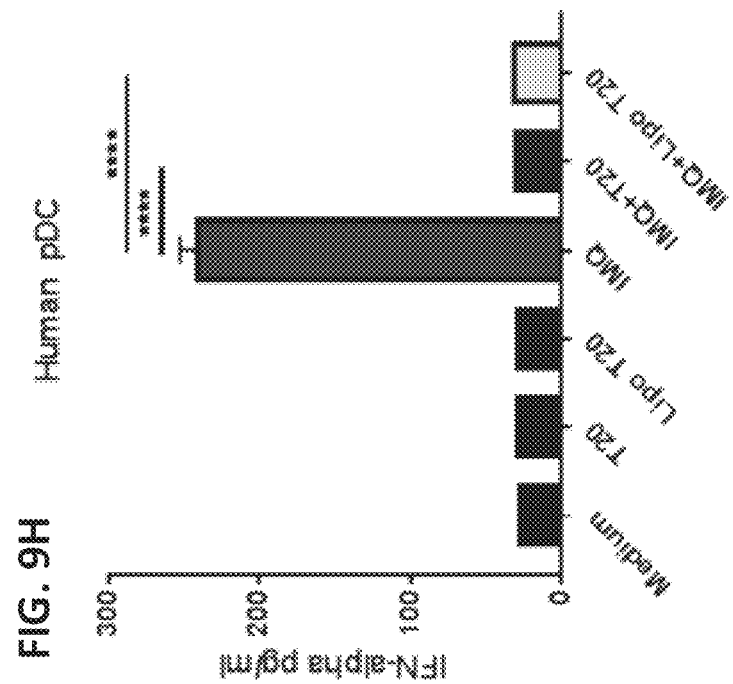
Figure 10B:
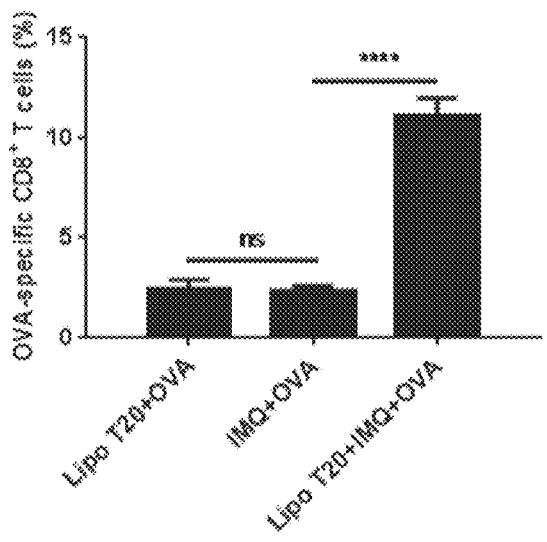
Figure 10C:
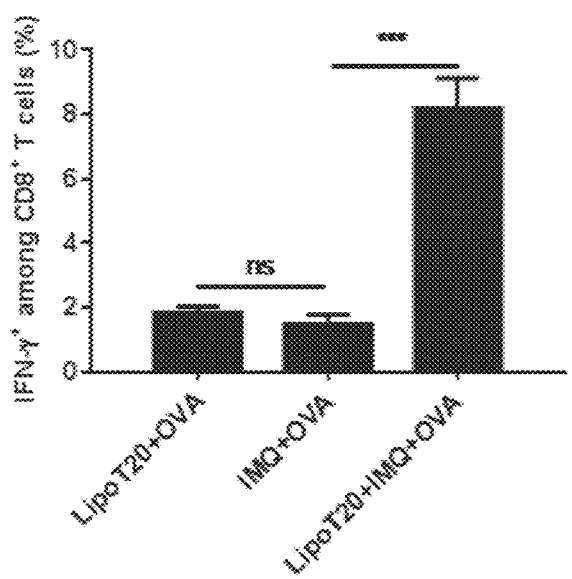
Figure 10D:
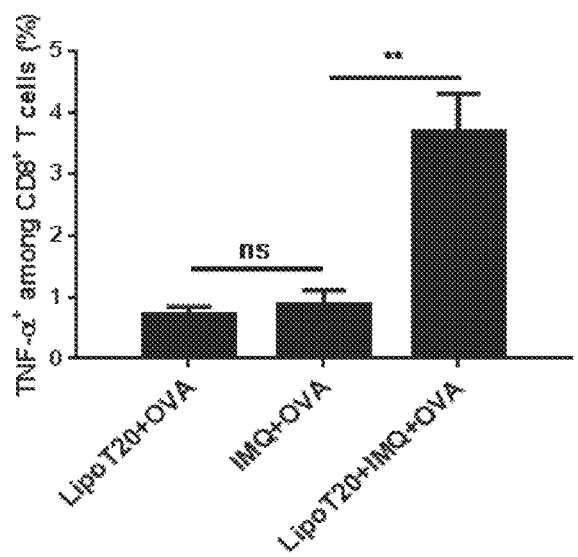
Figure 10E:
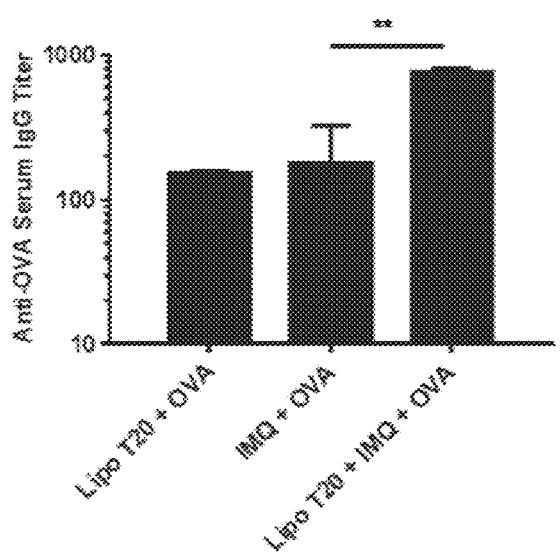
Figure 11A:
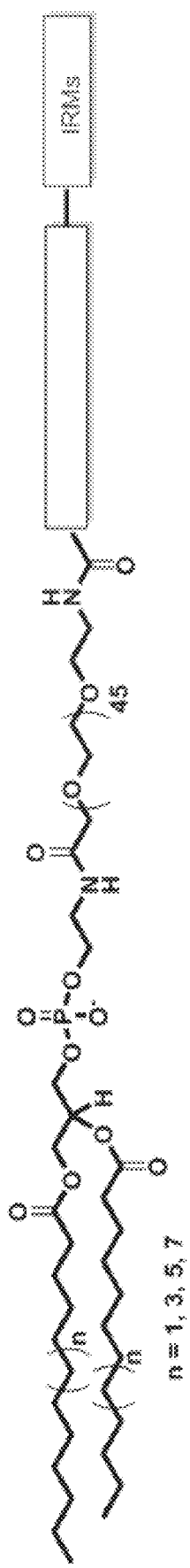
FIGS. 11A-11B.
Figure 11B:
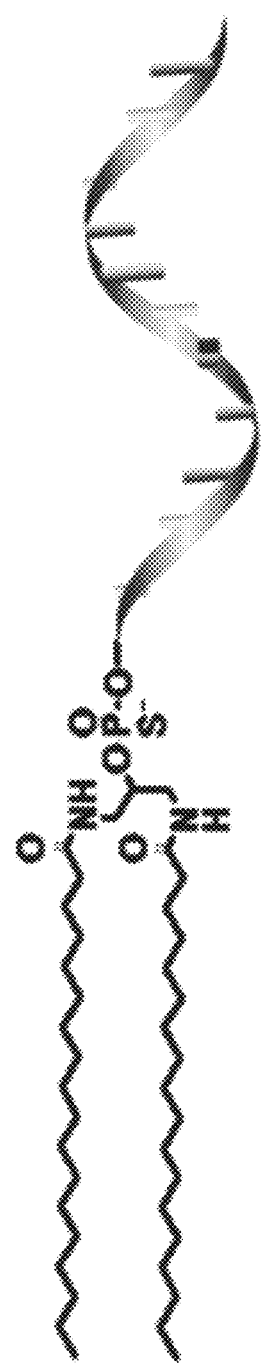

Using human pDC enriched from human PBMC with 55.7% purity (FIG. 9G), lipo T20 was further confirmed to partially conserve T20's capability of downregulating TLR7-mediated activation, evidenced by almost no secretion of IFN-α from pDC treated with IMQ and lipo T20 (FIG. 9H). Interestingly, it was observed that lipo T20 was able to significantly increase the production of TNF-α when mixed with TLR8-506 to treat human PBMC (FIG. 9I). However, lipo T20 was demonstrated to have no impact on TLR8-mediated NF-κB activation which regulated the production of pro-inflammatory cytokines including TNF-α. Although underlying mechanisms remained unknown, one possible interpretation was that lipo T20 mixed with TLR8 ligand might simultaneously activate various immune cells in PBMC, which led to TLR8-mediated NF-κB activation. These data emphasized specific innate immune activation pathways that lipo T20 possibly acted on. These results also suggest that lipo T20 could be a dual-booster for TLR7 and TLR8 adjuvants, which might be applied in clinical practice.

3.6 Adjuvant Booster (Lipo ODNs) Enhances the IRM Adjuvanted Immune Responses to Protein Antigen in Mice As described herein, lipo T20 improved the stimulatory potency and efficacy of IMQ in the presence of albumin. In fact, interstitial space in the body harbors considerable serum albumin that circulates through the lymphatic system and back to bloodstreams (Ikomi et al., *Annals of vascular diseases* 5, 258-268, 2012). Therefore, lipo T20 theoretically is able to hijack interstitial albumin and then leverage it for intensifying the potency of TLR7/8 ligands in the LNs. Previous studies reported that unmodified IMQ showed little accumulation in the LNs while lipo T20 was able to target APCs in the LN via 'albumin-hitchhiking' (Liu et al., *Nature* 507, 519-522, 2014; Lynn et al., *Nature Biotech* 33, 1201, 2015). Besides, the data described herein showed that lipo T20 amplified IMQ-induced immune activation in TLR reporter cells. Thus, it was hypothesized that subcutaneous administration of lipo T20 would improve the adjuvant effect of IMQ and immune activation. To test this hypothesis, mice were immunized with model antigen ovalbumin (OVA) adjuvanted with a low dose of IMQ in the presence or absence of 6.2 nmol lipo T20. Unformulated IMQ+OVA did not elicit detectable antigen-specific CD8$^+$ T cells in blood, presumably due to the insufficient lymph node targeting of IMQ. However, the addition of lipo T20 resulted in an approximate five-fold increase in OVA-specific CD8$^+$ T cells and up to a four-fold expansion of IFN-γ-secreting and TNF-α-secreting CD8$^+$ T cells, as well as significantly improved OVA-specific IgG titers in mice (FIG. 10).

These results demonstrated that lipo T20 functions as a potent TLR7/8 adjuvant booster to potentiate immune responses induced by the molecular vaccine in vivo. Thus, mixing vaccine formulation with the amphiphilic adjuvant booster represents a novel and simple approach to amplify the immunogenicity of subunit vaccines. The concept of adjuvant enhancers can be immediately applied to current molecular vaccines adjuvanted by TLR7/8 ligands, providing a plug and play approach to catalyze the development of next-generation cancer vaccines.

4. Conclusions

In summary, the results reported herein show that lipid-modified oligonucleotide-based TLR7/8 inhibitors were able to improve the potency and efficacy of TLR7/8 ligands in the presence of albumin. These lipo ODNs could tolerate a wide range of sequences, but the structurally-optimized lipo poly (dT) (20-25 nucleotides) showed maximal enhancing effects. In addition, lipo T20 was also applicable to human cells and was able to enhance human TLR7- and TLR8-mediated NF-κB stimulation. However, lipo T20 still conserved the immunosuppressive capability of reducing TLR7-mediated production of IFN-α in both murine and human cells. More significantly, lipo T20 was proved to be a powerful adjuvant enhancer in enhancing the immune responses to molecular vaccines, as lacing subunit vaccine formulation with lipo T20 led to markedly improved cellular and humoral responses in mice. This finding might be broadly applicable in many current vaccines, for instance where both efficacy and safety are needed.

Figure 12:
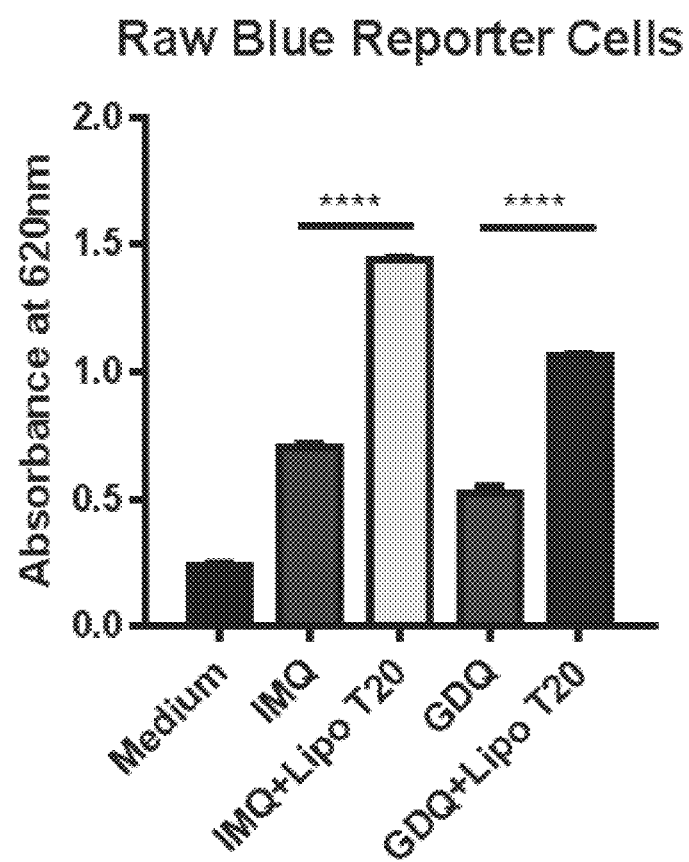
FIG. 12. Raw-Blue cells were stimulated with 4 µM (1 µg/ml) IMQ alone or plus 1 µM lipo T20, or 0.3 µM gardiquimod (0.1 µg/ml) GDQ alone or plus 1 µM lipo T20, for 24 h. Data show the mean values ±SEM. *, p<0.05; , p<0.01; *, p<0.001; ****, p<0.0001; ns, not significant by one-way ANOVA with Bonferroni post-test or unpaired Students' t-test.

Example 2: Lipid Conjugated Amphiphilic Oligodeoxynucleotide Improve Efficacy of Gardiquimod Using methods as described in Example 1, Gardiquimod (GDQ; FIG. 1A) was used to stimulate TLR7-mediated immune activation in Raw-Blue reporter cells, in the presence or absence of lipo T20. Similar to the results shown above with IMQ, lipo T20 at 1 μM was able to significantly enhance the immunostimulatory activities of GDQ (FIG. 12). This further illustrates that lipid conjugation can specifically reverse the inhibitory effect of oligonucleotide-based TLR7 inhibitors.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients, or components and to those that do not materially affect the embodiment. A material effect, in this context, is a statistically significant reduction in the adjuvant enhancing and/or immune stimulating function of a composition or method when compared to the composition or method without the unspecified element(s), step(s), ingredient(s), or component(s).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An amphiphilic oligonucleotide conjugate comprising:
   a lipophilic component comprising:
      a C14 diacyl lipid, a C18 diacyl lipid, a cholesterol, or

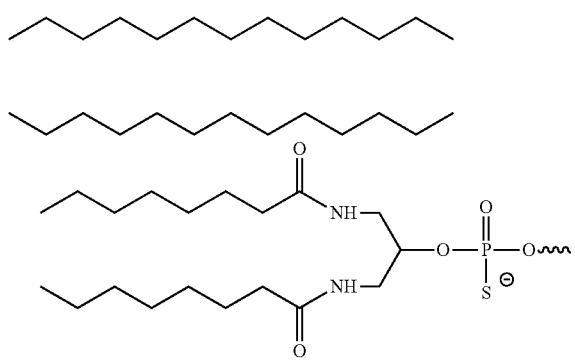

and
   directly or indirectly conjugated thereto, an immunomodulating oligonucleotide that, if it was not conjugated to the lipophilic component, would suppress TLR7 and/or TLR8 stimulation; the immunomodulating oligonucleotide comprising:
      a poly-oligo(dT) of 10-50 nucleotides (T10-T50), a poly-oligo(dT) of 20-25 nucleotides (T20-T25), or a sequence selected from SEQ ID NO: 1, SEQ ID NO: 2, SEQ ID NO: 3, and SEQ ID NO: 4.

2. The amphiphilic oligonucleotide conjugate of claim 1, wherein the lipophilic component is conjugated to the immunomodulating oligonucleotide at its 5' or 3' terminal end.

3. The amphiphilic oligonucleotide conjugate of claim 1, wherein the immunomodulating oligonucleotide comprises at least one phosphorothioate bond or at least one other modified (non-naturally occurring) bond.

4. The amphiphilic oligonucleotide conjugate of claim 1, further comprising a linker between the lipophilic component and the immunomodulating oligonucleotide.

5. The amphiphilic oligonucleotide conjugate of claim 1, comprising:

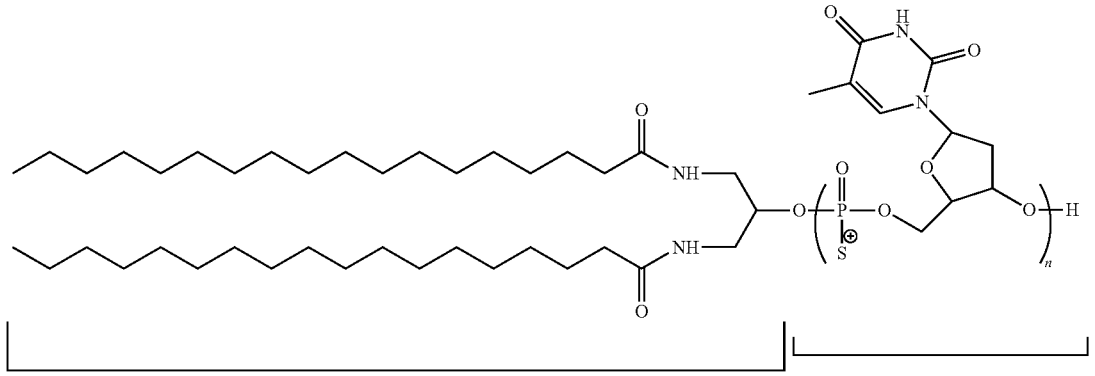

C18 Diacyl Lipid      5'--Poly Oligo(dT)n-3' wherein the value of n is 20; or

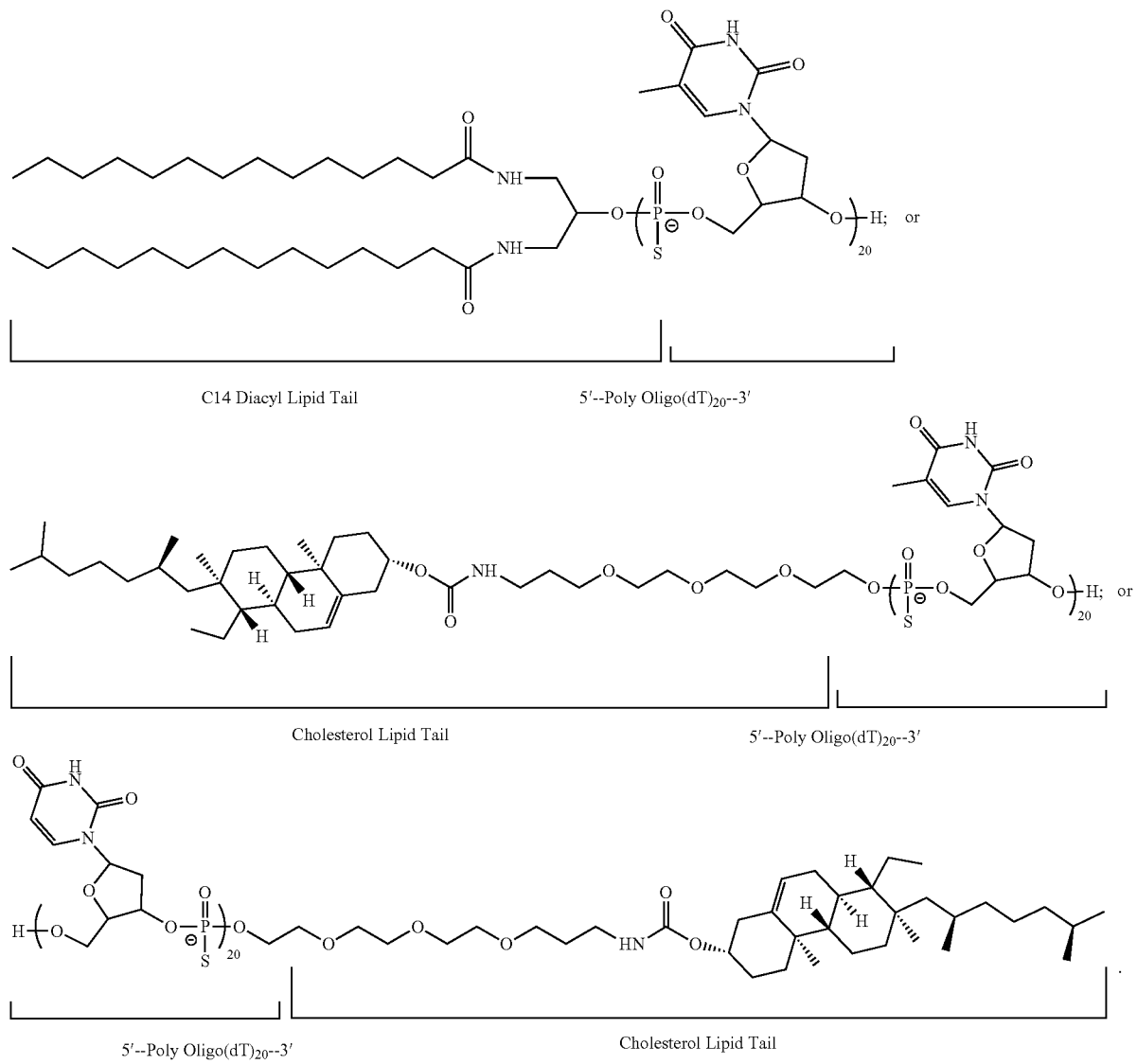

6. An immunogenic composition comprising:
an antigen;
a TLR7- or TLR8-mediated adjuvant; and
an amphiphilic oligonucleotide conjugate of claim 1.

7. The immunogenic composition of claim 6, further comprising at least one element of a delivery system.

8. The immunogenic composition of claim 6, wherein the antigen comprises a viral antigen, a bacterial antigen, a parasite antigen, an allergen, an environmental antigen, or a cancer antigen.

9. The immunogenic composition of claim 6, wherein the antigen comprises a subunit antigen.

10. The immunogenic composition of claim 6, further comprising at least one additional adjuvant.

11. The immunogenic composition of claim 6, wherein the TLR7- or TLR8-mediated adjuvant comprises a single-stranded RNA, an oligoribonucleotide (ORN), a base analog, or an imidazoquinolinamine.

12. The immunogenic composition of claim 11, wherein the imidazoquinolinamine is imiquimod (R-837; IMQ), resiquimod (R-848), or gardiquimod.

13. The immunogenic composition of claim 11, wherein the base analog comprises Loxoribine, CL075, CL097, CL264, CL307, or TLR8-506.

14. An enhanced adjuvant composition, comprising:
an adjuvant; and
the amphiphilic oligonucleotide conjugate of claim 1 in an amount sufficient to enhance an immune response to an antigen when the enhanced adjuvant composition is administered to a mammal.

15. A method of enhancing TLR-mediated activation in a subject in need thereof, comprising administering to the subject a therapeutically effective amount of the amphiphilic oligonucleotide conjugate of claim 1.

16. A method of improving therapeutic efficacy of an imidazoquinolinamine, comprising administering the imidazoquinolinamine concurrently with the amphiphilic oligonucleotide conjugate of claim 1.

17. The method of claim 16, wherein the imidazoquinolinamine is imiquimod (IMQ) or gardiquimod (GDQ).

18. The method of claim 17, wherein improving therapeutic efficacy of IMQ comprises inducing a higher level of NF-κB stimulation and/or promoting the secretion of proinflammatory cytokines.

19. A method of improving efficacy of a vaccine composition, comprising including in the composition the amphiphilic oligonucleotide conjugate of claim 1.

20. The method of claim 19, wherein improved efficacy comprises one or more of:
- increased immunostimulation,
- increased TLR7 stimulation,
- increased NF-κB activation in reporter cells,
- increased cytokine production in primary immune cells,
- lower $EC_{50}$,
- reduced toxicity,
- increased antigen-specific CD8 T cell response, and/or
- increased humoral response.

21. The method of claim 19, which occurs in vivo in the presence of albumin.

22. The method of claim 19, further comprising administering the vaccine composition to a mammalian subject.

* * * * *

UNITED STATES PATENT AND TRADEMARK OFFICE
CERTIFICATE OF CORRECTION

PATENT NO. : 11,504,425 B2  
APPLICATION NO. : 16/795953  
DATED : November 22, 2022  
INVENTOR(S) : Haipeng Liu et al.

Page 1 of 1

It is certified that error appears in the above-identified patent and that said Letters Patent is hereby corrected as shown below:

In the Claims

In Claim 5, at Column 41 & 42, Line 47-67, replace this structure:

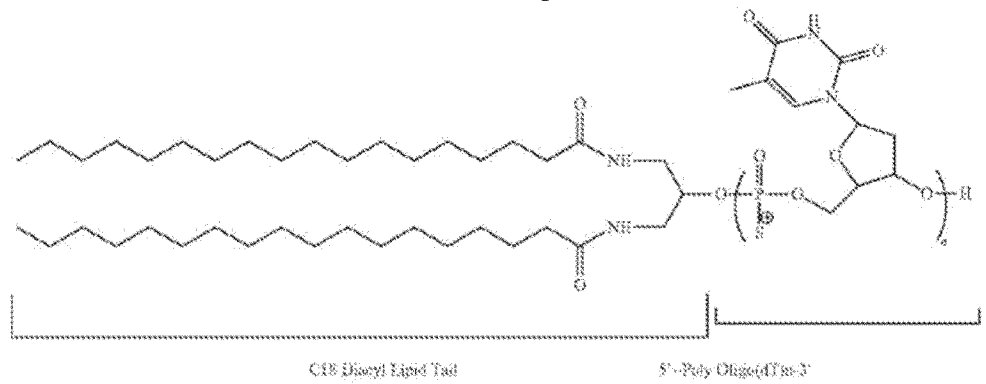

With the following correct structure:

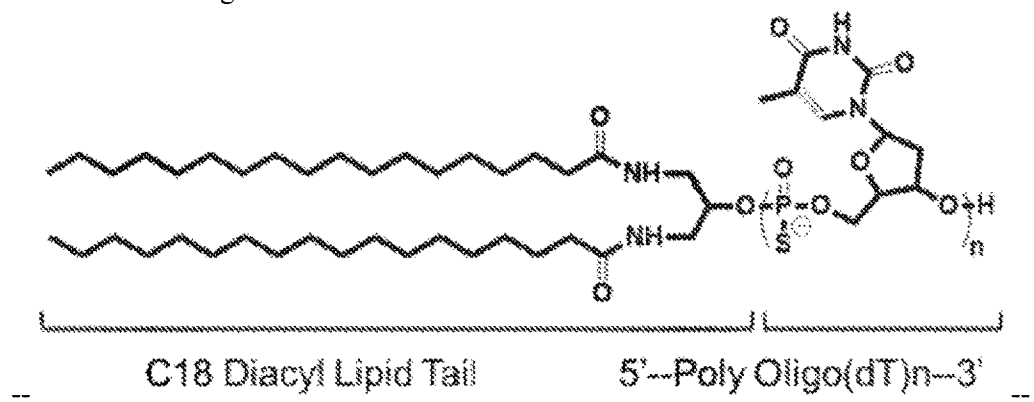

Signed and Sealed this  
Eighteenth Day of April, 2023

Katherine Kelly Vidal  
*Director of the United States Patent and Trademark Office*

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
tgctcctgga ggggttgt                                              18

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
tttttttttt tttttttttt                                            20

<210> SEQ ID NO 3
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 3
tcctgagctt gaagt                                                 15

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
tccatgacgt tcctgacgtt                                            20

<210> SEQ ID NO 5
<211> LENGTH: 8
<212> TYPE: PRT
<213> ORGANISM: Gallus gallus
<220> FEATURE:
<221> NAME/KEY: MISC_FEATURE
<222> LOCATION: (1)..(8)

```
<223> OTHER INFORMATION: Ovalbumin peptide OVA257-264, which is
      recognized by Antibody H-2Kb

<400> SEQUENCE: 5

Ser Ile Ile Asn Phe Glu Lys Leu
1               5

<210> SEQ ID NO 6
<211> LENGTH: 19
<212> TYPE: DNA
<213> ORGANISM: Artificial Sequence
<220> FEATURE:
<223> OTHER INFORMATION: Lipid-modified synthetic oligonucleotide
<220> FEATURE:
<221> NAME/KEY: misc_feature
<222> LOCATION: (1)..(1)
<223> OTHER INFORMATION: n=placeholder indicative of lipid portion of
      conjugate, as described in specification; lipid is variable,
      depending on embodiment(s)

<400> SEQUENCE: 6
ntgctcctgg aggggttgt                                                      19
```